(12) United States Patent
Degani et al.

(10) Patent No.: US 7,146,204 B2
(45) Date of Patent: Dec. 5, 2006

(54) METHOD AND APPARATUS FOR QUANTITATIVELY EVALUATING A KIDNEY

(75) Inventors: Hadassa Degani, Rehovot (IL); Maril Nimrod, Jerusalem (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 16 days.

(21) Appl. No.: 10/974,117

(22) Filed: Oct. 26, 2004

(65) Prior Publication Data
US 2005/0058598 A1 Mar. 17, 2005

Related U.S. Application Data

(63) Continuation of application No. PCT/US03/15238, filed on May 15, 2003.

(60) Provisional application No. 60/380,769, filed on May 15, 2002.

(51) Int. Cl.
*A61B 5/055* (2006.01)
(52) U.S. Cl. .................................................. 600/410
(58) Field of Classification Search ................ 600/407, 600/410, 419, 420; 128/920, 922
See application file for complete search history.

(56) References Cited

U.S. PATENT DOCUMENTS

| | | | | |
|---|---|---|---|---|
| 4,779,619 A | * | 10/1988 | Winkler | 600/410 |
| 5,303,705 A | * | 4/1994 | Nenov | 600/410 |
| 5,910,112 A | * | 6/1999 | Judd et al. | 600/410 |
| 6,681,132 B1 | * | 1/2004 | Katz et al. | 600/410 |
| 2002/0016543 A1 | * | 2/2002 | Tyler | 600/410 |
| 2002/0026116 A1 | * | 2/2002 | Schmainda | 600/419 |
| 2004/0204641 A1 | * | 10/2004 | Griffin | 600/410 |

OTHER PUBLICATIONS

US Dept of Health & Human Services, "Monitoring Renal Physiology and Pathology- Obtaining Sodium (23) Nuclear Magnetic Resonance Images of Human Kidney", 1988, Derwent-Acc-No. 1988-249608.*

* cited by examiner

*Primary Examiner*—Ruth S. Smith
(74) *Attorney, Agent, or Firm*—Martin Fleit; Paul D. Bianco; Fleit Kain Gibbons Gutman Bongini & Bianco P.L.

(57) ABSTRACT

A method and apparatus for monitoring a kidney that consists of monitoring the corticomedullary sodium concentration gradient in a kidney by an imaging technique selected from the group consisting of MRI, optical imaging, computed tomography (CT), ultrasound or positron emission tomography (PET), to obtain dynamic images; processing the obtained images to quantitatively determine, pixel by pixel of the images, the concentration of sodium along the corticomedullary axis of the kidney; and mapping the sodium distribution at high resolution to indicate the sodium concentration gradient of the corticomedullary axis of the kidney. Preferably the monitoring is carried out using $^{23}$Na MRI. Maps of the sodium distribution are displayed.

19 Claims, 18 Drawing Sheets

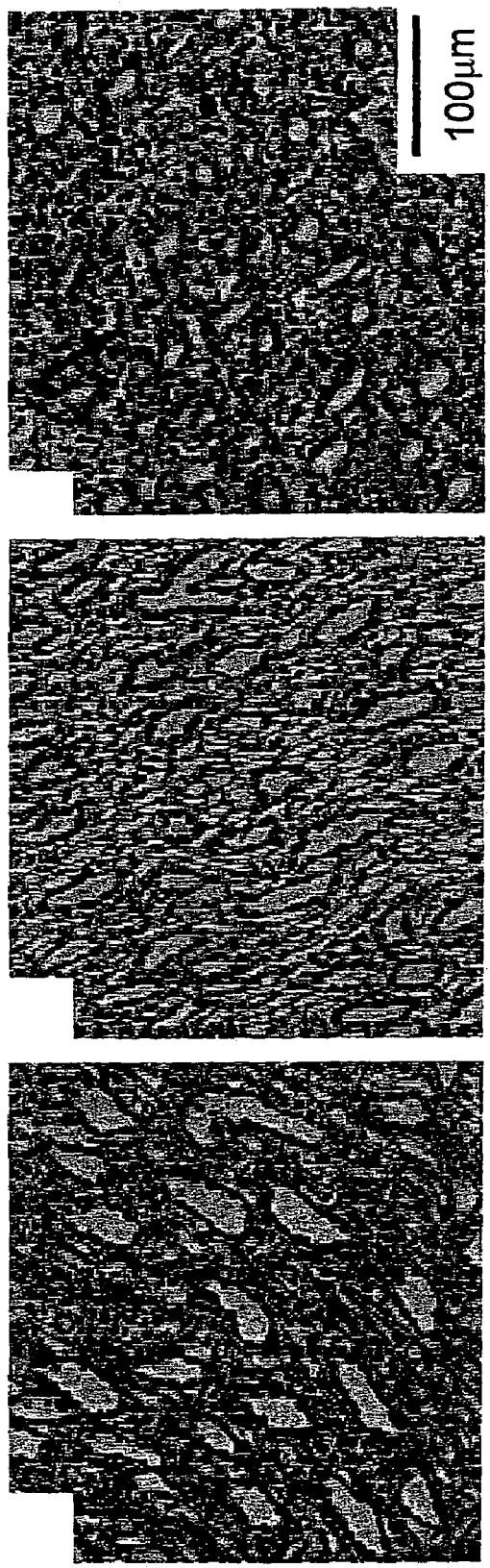

METHOD AND APPARATUS FOR QUANTITATIVELY EVALUATING A KIDNEY

CROSS REFERENCE TO RELATED APPLICATION

This application is a continuation of International Patent Application No. PCT/US03/15238, filed May 15, 2003, which is here incorporated by reference in its entirety.

BACKGROUND OF THE INVENTION

1. Field of the Invention

The present invention relates to a method and apparatus for quantitatively evaluating a kidney with respect to normal functioning, the effect of diuresis, and to detect any malfunction, including but not limited to hydronephrosis.

2. Prior Art

The major function of the kidney is to maintain body fluid and electrolyte homeostasis by filtering waste from the plasma and excreting the end products. Fluid homeostasis largely depends on the corticomedullary extracellular sodium concentration gradient. This gradient is maintained by a countercurrent mechanism, and serves as the driving force behind the reabsorption of water from the filtrate back into the plasma. Recently, based on a mathematical model of volume and solute microvascular exchange in the renal medulla, an exponential increase of sodium along the corticomedullary axis was hypothesized, Edwards A, Delong M J and Pallone T L. Interstitial water and solute recovery by inner medullary vasa recta. *Am. J. Physiol. Renal Physiol.* 278: F257–F269, 2000. This model supported the earlier electron microprobe data obtained by Koepsell et al. Measurements of exponential gradients of sodium and chlorine in the rat kidney medulla using electron microprobe. *Pflugers Arch.* 350: 167–184, 1974. However, the sodium concentration in the papilla reported by the latter authors was significantly higher than that determined in numerous other studies Azar S, Tobian L and Ishii M. Prolonged water diuresis affecting solutes and interstitial cells of renal papilla. *Am. J. Physiol.* 221: 75–79, 1971; Bengele H H, Mathias R S, Perkins J H and Alexander E A. Urinary concentrating defect in aged rat. *Am. J. Physiol.* 240: F147–F150, 1981; Buerkert J, Martin D, Prasad J and Trigg D. Role of deep nephrons and the terminal collecting duct in mannitol-induced diuresis. *Am. J. Physiol.* 240: F411–F422, 1981; Gennari F J, Johns C, Caflisch C R and Cortell S. Dissociation of saline-induced natiuresis from urea washout in the rat. *Am. J. Physiol.* 241: F250–F256, 1981; Jamison R L. The renal concentrating mechanism: micropuncture studies of the renal medulla. *Fed. Proc.* 42: 2392–2397, 1983; Martinez-Maldonado M, Eknoyan G and Suki W N. Influence of volume expansion on renal diluting capacity in the rat. *Clin. Sci. Mol. Med.* 46: 331–345, 1974; Pallone T L, Yagil Y and Jamison R L. Effect of small-solute gradients on transcapillary fluid movement in renal inner medulla. *Am. J. Physiol.* 257: F547–F553, 1989; Valtin H. Sequensration of urea and non urea solutes in renal tissues of rats with hereditary hypothalamic diabetes insipidus: effect of vasopressin and dehydration on countercurrent mechanism. *J. Clin. Invest.* 45: 337–345, 1966; and Wolff S D, Eng J, Berkowitz B A, James S and Balaban R S. Sodium-23 nuclear magnetic resonance imaging of the rabbit kidney in vivo. *Am. J. Physiol.* 258: F1125–F1131, 1990.

It is generally known that the sodium gradient is modified by administrating diuretic agents such as furosemide and mannitol, Suki W N, Stinebaugh B J, Frommer J P and Eknoyan G. Physiology of diuretic action. In: *The kidney; phydiology and pathophysiology.*, edited by Seldin D W and Giebisch G. New York: Raven Press, 1985, p. 2127–2162. Furosemide, a loop diuretic agent, exerts its influence by blocking the $Na^+/2Cl^-/K^+$ co-transporter located in the apical membrane of the thick segment of the medullar ascending limb. This co-transporter, together with the $Na^-/K^+/$ATPase pump in the basal membrane, extrudes sodium from the tubule to the interstitium. Thus, furosemide reduces the corticomedullary sodium gradient by inhibiting sodium reabsorption in the thick ascending limb, Puscheft J B. Pharmacological classification and renal actions of diuretics. *Cardiology* 84: 4–13, 1994. Mannitol, the osmotic diuretic agent most widely employed in the clinic, induces a decrease in renal vascular resistance, and an increase in extracellular fluid volume. These induced changes serve to amplify the medullar blood flow that "washes out" the excess sodium in the inner medulla, Better O S, Rubinstein I, Winaver J M and Knochel J P. Mannitol therapy revisited (1940–1997). *Kidney Int.* 51: 886–894, 1997. Although these two diuretics work are different, both decrease the sodium concentration in the inner medulla, Fraser A G, Cowie J F, Lambie A T and Robson J S. The effects of furosemide on the osmolality of the urine and the composition of the renal tissue. *J. Pharmacol. exp. Ther.* 158: 457–486, 1967; and Lote C J. *Principle of renal physiology.* London: Chapman & Hall, 1994.

Previous studies of sodium distribution in the kidney, and the diminution of the sodium concentration gradient following administration of furosemide and mannitol, Better O S, Rubinstein I, Winaver J M and Knochel J P. Mannitol therapy revisited (1940–1997). *Kidney Int.* 51: 886–894, 1997; and Puscheft J B. Pharmacological classification and renal actions of diuretics. *Cardiology* 84: 4–13, 1994; applied micropuncture, Buerkert J, Martin D, Prasad J and Trigg D. Role of deep nephrons and the terminal collecting duct in mannitol-induced diuresis. *Am. J. Physiol.* 240: F411–F422, 1981; and Jamison R L. The analytic methods used for the renal concentrating mechanism include: micropuncture studies of the renal medulla. *Fed. Proc.* 42: 2392–2397, 1983; radioautographic, Krakusin J S and Jennings R B. Radioautographic localization of 22-Na in the rat kidney. *A.M.A. Arc. Pathol.* 59: 471–486, 1955; and slice section, Bengele H H, Mathias R S, Perkins J H and Alexander E A. Urinary concentrating defect in aged rat. *Am. J. Physiol.* 240: F147–F150, 1981; and Atherton J C, Hai M A and Thomas S. The time course of changes in renal tissue composition during mannitol diuresis in the rat. *J. Physiol.* 197: 411–428, 1968. As these methods are invasive, it is of utmost importance to develop non-invasive means to monitor in vivo the spatial distribution of sodium in the kidney.

Obstructive uropathy caused by ureteric obstruction is one of the most common diseases of the urinary tract. Associated with this disorder are morphological changes of the urinary tract including a distended pelvic region with a flattened papilla, atrophy of renal parenchyma and hydroureter, Chuang, Y. H., W. L. Chuang, S. P. Huang, K. M. Liu, and C. H. Huang. The temporal relationship between the severity of hydroureter and the dynamic change of obstructed ureter in the rat model. *Br. J. Urol.* 76: 303–310, 1995. The extent of renal damage depends on the degree and duration of the obstruction, Leahy, A. L., P. C. Ryan, G. M. McEnttee, A. C. Nelson, and J. M. Fitzpatrick. renal injury and recovery in partial ureteric obstruction. *J. Urol.* 142: 199–203, 1989. In previous studies of uropathy in an animal model, using ureter ligation, changes were demonstrated in the morphology, haemodynamics and renal function of the hydronephrotic kidneys, Josephson, S., A. C. Ericson, and M. Sjoquist. Experimental obstructive hydronephrosis in newborn rats. *J. Urol.* 134: 391–395, 1985; Leahy, A. L., P. C. Ryan, G. M. McEnttee, A. C. Nelson, and J. M. Fitzpatrick. renal injury and recovery in partial ureteric obstruction. *J. Urol.* 142: 199–203, 1989; and Morsing, P., and E. G. Persson. Tubuloglomerular feedback in obstructive uropathy. *Kidney Int.* 39: S110–S114, 1991.

The most common techniques for monitoring obstructive pathology of the urinary tract have been intravenous urography and sonography, Brown, D. F., C. L. Rosen, and R. E. Wolfe. Renal ultrasonography. *Emerg. Med. Clin. North. Am.* 15: 877–893, 1997; Mustonen, S., I. O. Ala-Houala, P. Vehkalahti, p. Laippala, and T. L. J. Tammela. Kidney ultrasound and doppler ultrasound finding during and after acute urinary retention. *Eur. J. Ultrasound* 12: 189–196, 2001. Urography uses ionized radiation and i.v. injection of a contrast agent that may be harmful due to the potential nephrotoxicity of the contrast media, Katzberg, R. W. Urography into the 21st century: new contrast media, renal hendling, imaging characteristics, and nephrotoxicity. *radiology* 204: 297–312, 1997. Therefore patients with decreased renal function cannot be evaluated with CT. Although sonography is relatively sensitive for diagnosing obstruction, this method has difficulties in determining the extent of obstruction and cannot assess renal function, Brown, D. F., C. L. Rosen, and R. E. Wolfe. Renal ultrasonography. *Emerg. Med. Clin. North. Am.* 15: 877–893, 1997; and Rosi, P., G. Virgili, S. M. Di Stasi, A. Giurioli, B. Sensi, G. Vespasiani, and M. Porena. Diuretic ultrasound. A non-invasive technique for the assessment of upper tract obstruction. *Br. J. Urol.* 65: 566–569, 1990. More recently non-enhanced helical CT and dynamic contrast enhanced MRI using GdDTPA as a contrast agent has been evaluated in patients with suspected urinary obstruction, Chen, M. Y. M., and R. J. Zagoria. Can noncontrast helical computed tomography replace intravenous urography for evaluation of patients with acute urinary tract colic. *J. Emerg. Med.* 17: 299–303, 1999; and Wen, J. G., Y. Chen, S. Ringgaard, J. Frokiaer, T. M. Jorgensen, H. Stodkilde-Jorgensen, and J. C. Djurhuus. Evaluation of renal function in normal and hydronephrotic kidneys in rats using gadolinium diethylenetetramine-pentaacetic acid enhanced dynamic magnetic resonance imaging. *J. Urol.* 163: 1264–1270, 2000. However both methods do not provide detailed information about renal function in cases of complete obstruction. Consequently, it is up of important to look for a non-invasive and safe method for assessing the functionality of the obstruct kidney.

One of the key functions of the kidney is to maintain fluid homeostasis. This function depends on the sodium and urea concentration gradient between the cortex and the medulla. This gradient, achieved by the countercurrent mechanism, serves as a driving force for reabsorbing water from the filtrate back into the plasma, Jamison, R. L., and W. Kriz. *Urinary concentrating Mechanism.* New York Oxford: Oxford University Press, Inc., 1982. It has been suggested, at least on a quantitative basis that MRI of the sodium nucleus could provide a unique, non-invasive tool for monitoring renal function by mapping directly the sodium spatial distribution, Maeda, M., Y. Seo, M. Murakami, S. Kuki, H. Watari, S. Iwasaki, and H. Uchida. Sodium imaging of the kidney in the Guinea pig at 2.1 T, following arterial, venous, and ureteral ligation. *Magn. Reson. Med.* 16: 361–367, 1990; and Ra, J. B., S. K. Hilal, C. H. Oh, and I. K. Mun. In vivo magnetic resonance imaging of sodium in the human body. *Magn. Reson. Med.* 7: 11–22, 1988. Variations in the sodium distribution in the obstructed kidney may relate to the extent of kidney obstruction. Previous $^{23}$Na MRI of the kidneys in rodents has demonstrated qualitatively the capacity of this method to detect the sodium gradient and to monitor changes in this gradient as a result of saline infusion, Bansal, N., and V. Seshan. Three-dimensional triple quantum filtered 23-Na imaging of rabbit kidney with weighted signal averaging. *J. Magn. Reson. Imag.* 5: 761–767, 1995; Wolff, S. D., C. Eng, and R. S. Balaban. NMR studies of renal phosphate metabolites in vivo: effects of hydration and dehydration. *Am. J. Physiol.* 255: F581–F589, 1988; and Wolff, S. D., J. Eng, B. A. Berkowitz, S. James, and R. S. Balaban. Sodium-23 nuclear magnetic resonance imaging of the rabbit kidney in vivo. *Am. J. Physiol.* 258: F1125–F1131, 1990.

SUMMARY OF THE INVENTION

Accordingly, the object of the present invention is to provide a method and apparatus for quantitatively examining renal sodium concentration using a non-ionizing technique based on nuclear magnetic resonance (NMR). By practice of the invention, magnetic resonance imaging (MRI) of the sodium nuclei enabled determination of the spatial distribution of renal sodium in detail, and to precisely monitor changes in this distribution over time. In particular, the present invention enabled determination of a detailed evaluation of the sodium concentration along the corticomedullary axis, which was correlated with histological findings. The results have indicated the capacity of the invention to function non-invasively to characterize the extent of obstruction and the residual function of the kidney in a quantitative manner.

The present invention enables confirmation of the fact that renal function is highly correlated with the sodium concentration gradient along the corticomedullary axis. In accordance with the practice of the method and apparatus of the present invention the application of 3D magnetic resonance imaging (MRI) enables the determination of this gradient in an intact kidney by direct, non-invasive detection of its sodium content under normal and diuretic conditions. Moreover, the present invention enables the monitoring of rapid changes in gradient induced by mannitol and furosemide diuresis.

The results obtained by the use of the invention clearly demonstrated a linear increase of sodium along the corticomedullary axis of 74±9 mM×mm$^{-1}$ in control kidney, reaching in the inner medulla to a sodium concentration, which is fourfold higher than that in the cortex. After a bolus injection of furosemide or mannitol, the corticomedullary gradient was markedly modified, with a 50% reduction in sodium content in the inner medulla for both diuretics. However, mannitol-induced sodium reduction occurred twice as rapidly as that induced by furosemide. Furthermore, a detailed, pixel-by-pixel analysis of the cortical-outer medullar gradient revealed, with unprecedented clarity, that sodium concentration was modulated by each diuretic in a different manner. Mannitol, an osmotic diuretic, did not affect the cortical-outer medullar sodium gradient whereas with furosemide, a loop diuretic, induced a five-fold reduction in this gradient. These differences serve to point up specific functional changes associated with the different mechanisms and sites of action of these two diuretics. The present invention enables use of sodium MRI as a non-invasive clinical tool for functional imaging of the kidney.

Magnetic Resonance Imaging (MRI) of $^{23}$Na at high spatial resolution provides a non-invasive, quantitative means to assess renal function through measurement of the corticomedullary sodium concentration gradient. By the present invention the application of this approach to specifically characterize in vivo spontaneous and experimental acute hydronephrosis in a kidney, and more particularly, in a rat kidney. Pixel by pixel analysis along the corticomedullary axis revealed marked differential changes in the linear sodium gradient (73±4 mM×mm$^{-1}$) due to the different forms of hydronephrosis: The sodium gradient from the cortex to the outer medulla remained unaltered in spontaneous hydronephrosis and decreased by more than twofold in experimental acute hydronephrosis. In both forms of hydronephrosis, the sodium content in the inner region of the kidney was abruptly reduced, leading to an inverse sodium gradient from the outer medulla to the papilla. Histology examinations indicated similar total size of the parenchyma in the two forms of hydronephrosis. However, microscopic inspection revealed a clear tubular damage in the acute hydronephrosis but not in the spontaneous one. The lack of differentiation at the macro level infers the limitation of solely anatomical imaging and the necessity of functional sodium imaging to differentiate between these two types of hydronephrosis. In addition, The invention obtained results demonstrating the capacity of $^{23}$Na MRI to detect and measure the extent of the residual function in the obstructed kidney.

The foregoing objects, results and advantages of the present invention are accomplished by a novel method for monitoring a kidney comprising the steps of:

a. monitoring the corticomedullary sodium concentration gradient in a kidney by an imaging technique selected from the group consisting of MRI, optical imaging, computed tomography (CT), ultrasound or positron emission tomography (PET), to obtain dynamic images;

b. processing the obtained images to quantitatively determine, pixel by pixel of the images, the concentration of sodium along the corticomedullary axis of the kidney; and c. mapping the sodium distribution at high resolution to indicate the sodium concentration gradient of the corticomedullary axis of the kidney.

In the foregoing method, it is preferred that the method be conducted wherein the monitoring is carried out using $^{23}$Na MRI.

The invention further contemplates a novel apparatus for monitoring a kidney comprising: 1) a monitor for determining the corticomedullary sodium concentration gradient in a kidney by an imaging technique selected from the group consisting of MRI, optical imaging, computed tomography (CT), ultrasound or positron emission tomography (PET), to obtain dynamic images; 2) a processor for processing the obtained images to quantitatively determine, pixel by pixel of the images, the concentration of sodium along the corticomedullary axis of the kidney; and 3) a mapper for mapping the sodium distribution at high resolution to indicate the sodium concentration gradient of the corticomedullary axis of the kidney. The apparatus can further including a display for portraying maps of the sodium distribution.

Other and further objects and advantages of the present invention will become evident from the following detailed description of preferred embodiments of the invention when taken in conjunction with the appended drawings.

BRIEF DESCRIPTION OF THE FIGURES OF THE DRAWING

FIG. 2A shows a typical example of the change in sodium concentration along the corticomedullary axis versus the distance from the cortex measured, using a pixel-by-pixel analysis. FIG. 2B shows average sodium concentration±SEM in the different regions of the kidney using the ROI of the cortex (Cor), outer medulla (OM), and inner medulla (IM) (n=17).

FIGS. 4A and 4C show furosemide-induced changes in the inner medulla and cortex, respectively. FIGS. 4B and 4D show mannitol-induced changes in the inner medulla and the cortex, respectively. Kinetics was more rapid during mannitol diuresis than during furosemide diuresis.

FIG. 5C shows average sodium concentration±SEM relative to that of the cortex, calculated from the sodium images, for the different kidney regions: Cortex (Cor), outer medulla (OM), and inner medulla (IM). Gray column: Control (n=7). Black column: Diuresis steady state (n=7).

FIG. 6C shows average sodium concentration±SEM relative to that of the cortex, calculated from the sodium images for the different kidney regions: Cortex (Cor), outer medulla (OM), and inner medulla (IM). Gray column: Control (n=7). Black column: Diuresis steady state (n=7).

FIG. 7A—Mannitol and FIG. 7B—furosemide. Sodium concentrations relative to that in the cortex at control steady state (O) and diuresis steady state (●) versus the distance from the cortex, measured using a pixel-by-pixel analysis of the sodium images as described hereinafter.

FIG. 9B shows a typical example of the change in sodium concentration along the corticomedullary axis, versus the distance from the cortex measured, using a pixel-by-pixel analysis on the image in FIG. 9A.

FIGS. 13A to 13I show photomicrographs of hematoxilin-eosin stained section of renal cortex (FIGS. 13A, 13B and 13C) outer medulla (FIGS. 13D, 13E and 13F) and inner medulla (13G, 13H and 13I) of the control kidney (FIGS. 13A, 13D and 13G), spontaneous hydronephrotic kidney FIGS. 13B, 13H and 13G) and acute hydronephrotic kidney (13F, 13I and 13G). The spontaneous hydronephrotic kidney shows normal glomeruli and tubules. The acute hydronephrotic kidney shows mark dilation (white arrows) and tubular damage (dark arrows).

DETAILED DESCRIPTION OF PREFERRED EMBODIMENTS OF THE INVENTION

Figure 1:
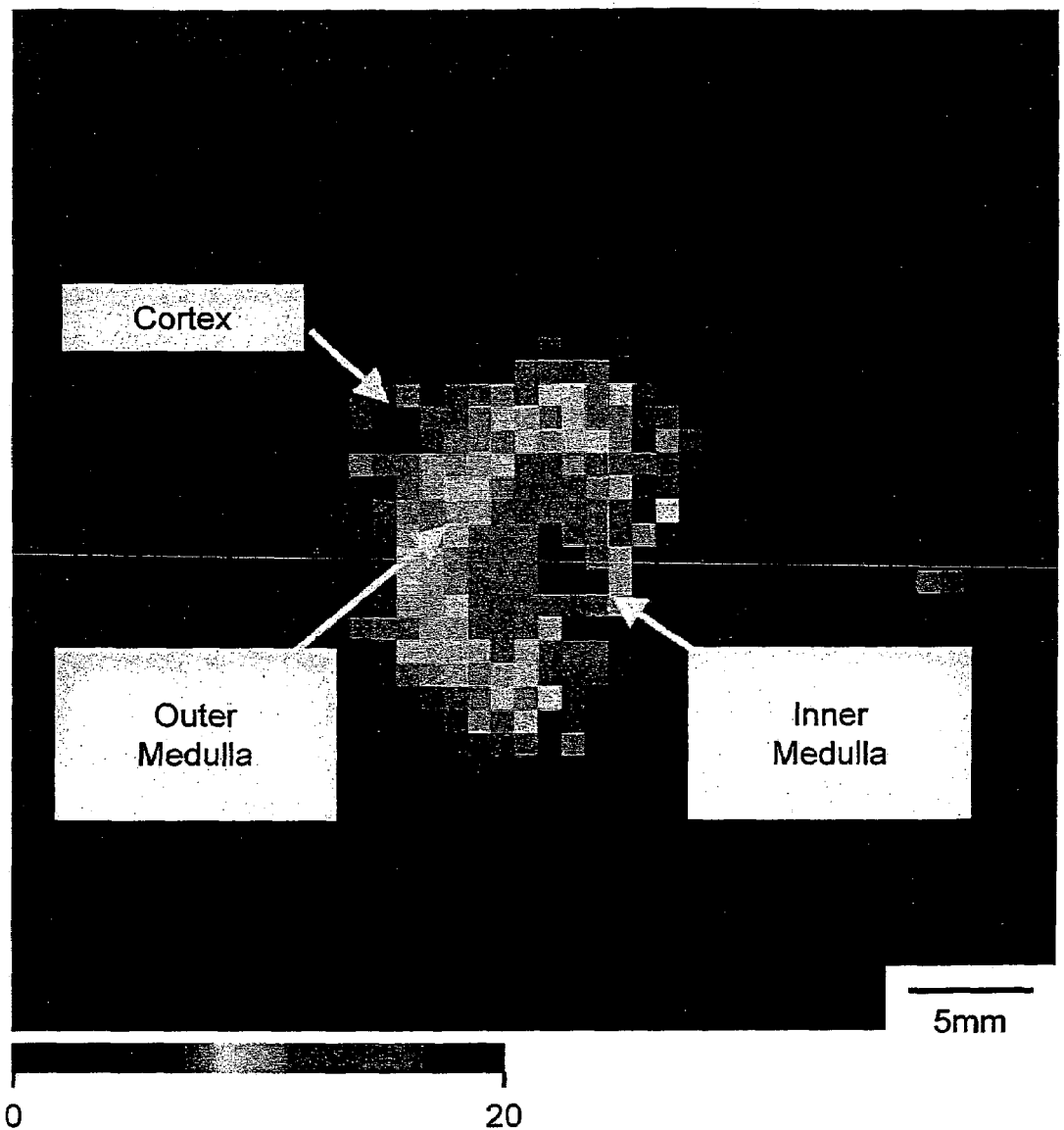
FIG. 1 shows a coronal $^{23}$Na image of the right kidney in a female Lewis rat. The image shows an increase in sodium signal intensity from the cortex to the inner medulla. The image was recorded using a 3D gradient echo sequence with TE/TR of 3.1/60 ms, spatial resolution of 0.974×0.974×5 mm and 20 min scanning time.

MRI of the water protons using various techniques has been applied as a non-invasive tool for assessing renal function, Bennet H F and Li D. MR imaging of renal function. *Magn. Reson. Imaging Clin. N. Am.* 5: 107–126, 1997; and Knesplova L and Krestin G P. Magnetic resonance in the assessment of renal function. *Eur. Radiol.* 8: 201–211, 1998. For example, the loss of contrast that provided corticomedullary differentiation in $T_1$-weighted MR images served as a non-specific indicator of renal pathology, Marotti M H H, Terrier F, McAninch J W, Thuroff J W. MR in renal disease: importance of cortical-medullary distinction. *Magn Reson Med* 5: 160–172, 1987; and Stark D D and Bradley jr W G. *Magnetic resonance imaging*. St. Louis: Mosby year book, 1992. Functional MR studies using dynamic contrast-enhanced imaging have also been used to evaluate renal vasculature, perfusion and tubular concentration ability Knesplova L and Krestin G P. Magnetic resonance in the assessment of renal function. *Eur. Radiol.* 8: 201–211, 1998.

Unlike proton ($^1$H) MRI, there are only a few renal sodium ($^{23}$Na) MRI studies. The ability of sodium MRI to detect precisely the renal sodium signal has been demonstrated by scanning the abdomen of guinea pigs, Maeda M, Seo Y, Murakami M, Kuki S, Watari H, Iwasaki S and Uchida H. Sodium imaging of the kidney in the Guinea pig at 2.1 T, following arterial, venous, and ureteral ligation. *Magn. Reson. Med.* 16: 361–367, 1990; and humans, Ra J B, Hilal S K, Oh C H and Mun I K. In vivo magnetic resonance imaging of sodium in the human body. *Magn. Reson. Med.* 7: 11–22, 1988. $^{23}$Na NMR of the exposed rat kidney using the rotating-frame method demonstrated higher sodium signal in the outer medulla, relative to the other regions of the kidney, Bogusky R T, Garwood M, Matson G B, Acosta G, Cowgill L D and Schleich T. Localization of phosphorous metabolites and sodium ions in the rat kidney. *Magn. Reson. Med.* 3: 251–261, 1986. $^{23}$Na MRI studies of the exposed rabbit kidney demonstrated a three- to fivefold higher sodium content in the papilla relative to the cortex, and enabled monitoring of changes in the sodium gradient following saline infusion, Wolff S D, Eng J, Berkowitz B A, James S and Balaban R S. Sodium-23 nuclear magnetic resonance imaging of the rabbit kidney in vivo. *Am. J. Physiol.* 258: F1125–F1131, 1990; Wolff S D, Eng C and Balaban R S. NMR studies of renal phosphate metabolites in vivo: effects of hydration and dehydration. *Am. J. Physiol.* 255: F581–F589, 1988; and Bansal N and Seshan V. Three-dimensional triple quantum filtered 23-Na imaging of rabbit kidney with weighted signal averaging. *J. Magn. Reson. Imag.* 5: 761–767, 1995.

The present invention concerns the renal function of the kidney. In the present invention, investigations and studies were made of the renal function in rats, the most common animal model for studies of this organ. Utilized were high-resolution 3D-sodium MRI to characterize in detail the corticomedullary sodium gradient, and its specific modulation under conditions of diuresis induced by furosemide and mannitol. Both dynamic and spatial changes in sodium distribution along the corticomedullary axis reflected the different mechanisms of action and sites of activity of these two agents, revealing the potentially high specificity of sodium MR renography. This work therefore served as a predicate for the development of clinical functional sodium MRI, as being of particular value due to its non-invasive nature.

Materials and Methods—Animals: Studies were performed on female Lewis rats, 2–4 months old and weighing 250–300 g, that had free access to food and water. Before MRI scanning, the rats were anesthetized by an intraperitoneal injection of sodium pentobarbital at a dosage of 0.04 mg/g body wt. All animal protocols and maintenance procedures were in accordance with the guidelines of the Committee on Animals of the Weizmann Institute of Science, and were approved by this Committee.

Diuretics: A solution of 10 mg/ml furosemide (Hoechst, Germany) was injected as a bolus into the tail vein of the rat, in three different doses: 1, 3, and 10 mg/kg body wt. Mannitol solution (20%, 1 ml) and saline solution (0.9% NaCl, 1 ml) were injected as a bolus into the tail vein. Only one diuretic was injected into each rat.

Urine sodium: Urine samples of untreated (control) and diuretic rats were collected in a metabolic cage. Collection of the urine from the diuretic rats started 15 minutes after injection of the diuretic, when the urine flow was constant. The urine samples were then centrifuged, and the supernatants transferred to a 5 mm NMR tube placed in the center of a 10 mm NMR tube. The external tube was used as an external reference, and contained a solution of 120 mM NaCl and 5 mM of the shift reagent: thulium (III) 1,4,7,10-tetraacyclododecane-1,4,7,10-tetrakis (methylene phosphonate) (TmDOTP$^{5-}$) (Macrocyclics, Dallas, Tex., USA) reaching total [Na$^+$] of 150 mM. $^{23}$Na NMR spectra were recorded with a Bruker DMX-400 spectrometer (Bruker, Rheinstetten, Germany), using a multinuclei broad band probe at 106 MHz by acquiring 10 transients with 90° pulses, pulse-to-acquisition time of delay (DE) of 6 μs, 0.47 sec repetition time (TR) and 0.27 sec acquisition time. Analysis of the $^{23}$Na spectra was performed with an XWIN-NMR Bruker software package. Sodium concentration in the urine was calculated from the integrated area of its signal referenced to the integrated area of the shifted signal of the sodium in the external tube solution (150 mM).

In vivo MRI: $^1$H and $^{23}$Na spectra and images were recorded at 200 and 53 MHz, respectively with a 4.7 T Biospec spectrometer (Bruker, Rheinstetten, Germany) using a home-built 3 cm double-tuned surface coil. The rat was placed on the coil in a supine position, keeping the estimated kidney position approximately in the middle of the coil. 3D $^1$H gradient echo images were recorded to localize the exact kidney position, using TE/TR of 6/30 ms FOV of 12×12×3.2 cm and a matrix of 256×256×32. For defining the regions of interest (ROI), 3D $^1$H images were recorded with the same spatial resolution as that of the sodium images.

In the "steady state" studies, sodium images were recorded prior to injection of the diuretic (control measurement) and fifteen minutes after its injection. 3D $^{23}$Na gradient echo images were recorded using a TE/TR of 3.1/60 ms and a 90° OSIRREAD adiabatic pulse, FOV of 12×12×8 cm, and a matrix of 128×128×16 with 10 or 20 scans (20 or 40 min, respectively).

In the dynamic studies, sequential 3D $^{23}$Na gradient echo images were recorded prior to injection of the diuretic (control measurement) and every 2 or 4 min after the injection of mannitol or furosemide, respectively, using TE/TR of 1.7/60 ms and FOV of 16×16×8 cm with 2–4 scans (2–4 min, respectively). The MR visibility of the sodium nuclei in the kidney was evaluated in reference to a standard of 9% saline solution contained in a sealed plastic tube that was transplanted near the kidney and imaged as above.

Image analysis: Analysis of the kidney images was performed on selected regions of interest (ROIs) in the outer, median and inner parts of the kidney, representing the cortex, outer and inner medulla, respectively. The ROIs were defined on the corresponding coronal proton image recorded prior to the sodium images, at the same spatial resolution. The average digitized pixel intensity for each ROI was measured, and the sodium gradient was assessed by averaging the ratio of the sodium signal intensity between the inner and the outer medulla, and between the inner medulla and the cortex. The results present average values for the number of measured kidneys±standard error.

In addition, a pixel-by-pixel analysis was performed, in order to assess the behavior of the NMR sodium signal along the corticomedullary axis. In this analysis, the signal intensity in each pixel was measured from the cortex to the inner medulla along the corticomedullary axis. This yielded a graph of pixel signal intensity versus the distance of the pixel from the cortex. In the dynamic study, the average signal intensities of the inner medulla and the cortex ROIs, defined on the proton image, were measured in sodium images recorded sequentially and were then plotted against time.

In vivo $^{23}$Na spectroscopy: $^{23}$Na NMR was performed with the same surface coil as described above. The rat was placed on the coil, keeping the estimated left kidney position approximately in the middle of the coil. The shimming of the magnetic field was performed on the proton signal. A T$_1$ weighted fast $^1$H gradient echo image was recorded at 200 MHz as described above, to ensure that the left kidney was in the middle of the surface coil. The coil was then tuned to 53 MHz, and the sodium spectra were recorded by acquiring 40 transients, 0.6 sec repetition time and 0.12 sec acquisition time. A short 6 μs interval between the 90° pulse and the acquisition was applied. This ensured detection of the short T$_2$ component of the sodium signal (0.5–2.5 ms), yielding ~100% MR visibility for $^{23}$Na. Sequential spectra were recorded prior to (n=5) and following (n=15) the administration of diuretics, with a 3 min interval between them. Analysis of the $^{23}$Na spectra was performed with an XWIN-NMR Bruker software package.

Statistical analysis to evaluate differences between pixels or ROIs in the same kidney, or before and after diuretic treatment, were performed by a two-tailed paired Student's t-test; otherwise, the unpaired version of this test was used. Results are presented as mean±SEM.

Results: The corticomedullary sodium gradient: Sodium images recorded in control rats revealed gradual changes in the intensity of the sodium signal in the kidney, with the signal increasing from the cortex through the medulla, and reaching its highest intensity in the inner medulla (FIG. 1). Pixel-by-pixel measurement along the corticomedullary axis showed a linear increase in signal intensity, with a slope of 0.51±0.06 a.u.×mm$^{-1}$ (R=0.97±0.01, n=17). This gradient remained unchanged for TR varying from 50–400 ms, and TE from 1.7 to 6 ms, indicating non-saturation conditions and similar T$_1$ and T$_2$ relaxation times of $^{23}$Na throughout the entire kidney, as was previously reported, Wolff S D, Eng J, Berkowitz B A, James S and Balaban R S. Sodium-23 nuclear magnetic resonance imaging of the rabbit kidney in vivo. *Am. J. Physiol.* 258: F1125–F1131, 1990.

Figure 2A:
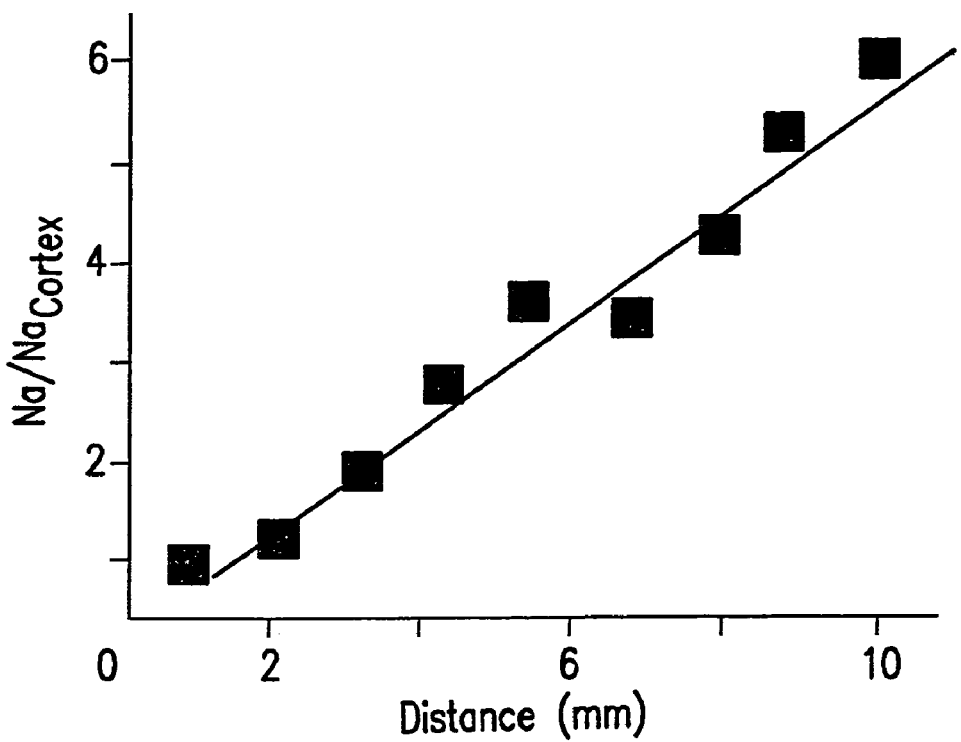
FIGS. 2A and 2B shows image analysis of the sodium gradient in the intact rat kidney.
Figure 2B:
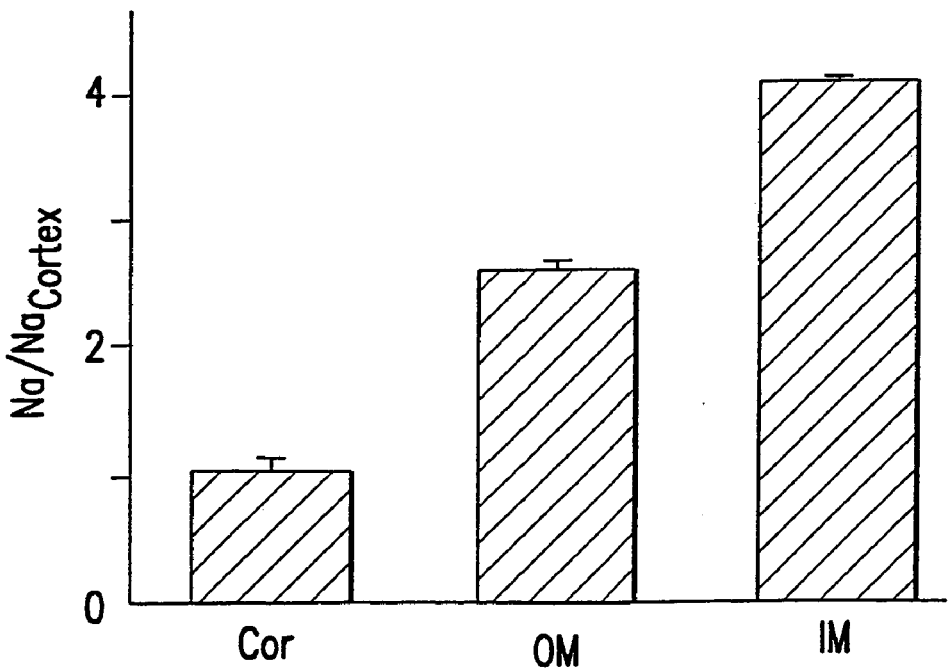

Based on the common assumption that the concentration of sodium in the cortex is equal to that in the plasma [Jamison R L and Kriz W. *Urinary concentrating Mechanism*. New York Oxford: Oxford University Press, Inc., 1982 and references cited therein], and predicting similar visibility of sodium through the entire kidney, it was possible to convert the signal intensity units to concentration units, thereby obtaining a linear corticomedullary sodium gradient of 74±9 mM×mm$^{-1}$ (FIG. 2A). In addition, the regional sodium gradient was calculated using an ROI-based analysis, taking into account the internal symmetry of each kidney region, (see Materials and Methods, supra). This analysis yielded an inner medulla sodium content, which is 1.6±0.1 higher than that in the outer medulla and 4.1±0.1 higher than that in the cortex (FIG. 2B, n=17).

As the intensity of the sodium MR signal in tissues depends on the concentration and the visibility of this nucleus, Boulanger Y and Vinay P. Nuclear magnetic resonance od sodium in biological tissues. *Can. J. Physiol. Pharmacol.* 67: 820–828, 1989, the visibility of the sodium signal was determined under the experimental conditions. This assessment involved implanting a sealed saline tube near the kidney, and simultaneously measuring the sodium signal intensity in the tube and in the kidney. As mentioned in the previous paragraph, the concentration of sodium in the cortex is 145 mM; hence, the intensity of the sodium signal in the cortex, relative to the free saline solution in the tube, yielded a visibility of 46±1% (n=3).

Figure 3B:
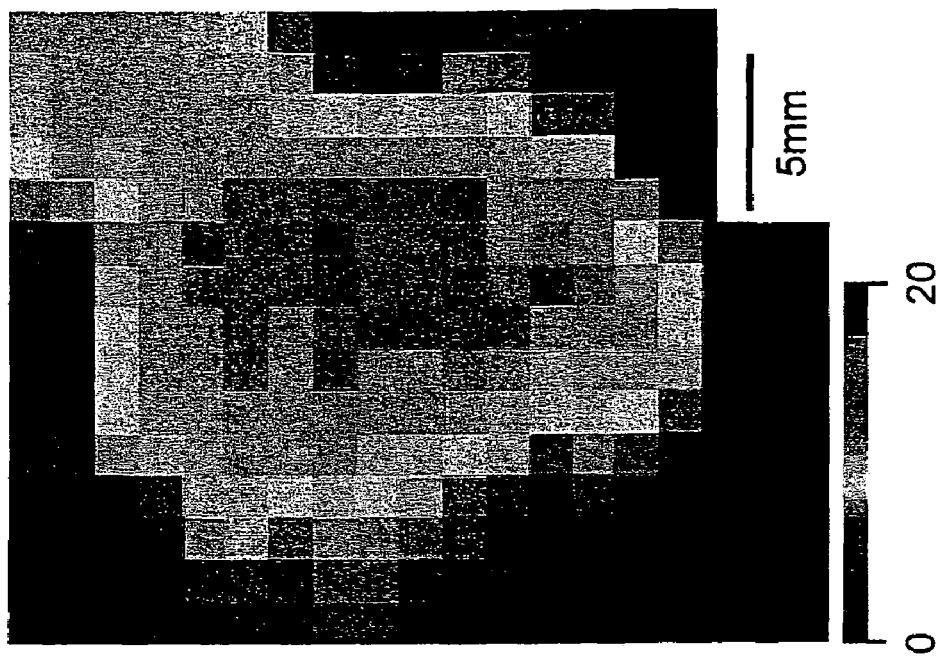
FIGS. 3A and 3B show furosemide-induced changes in sodium distribution in the kidney. Typical sodium images obtained in a dynamic study before are shown in FIG. 3A and 8 min after in FIG. 3B a bolus injection of 10 mg/kg body wt furosemide. Images were recorded using TE/TR of 1.7/60 ms, with spatial resolution of 1.25×1.25×5 mm and temporal resolution of 4 min.
Figure 3A:
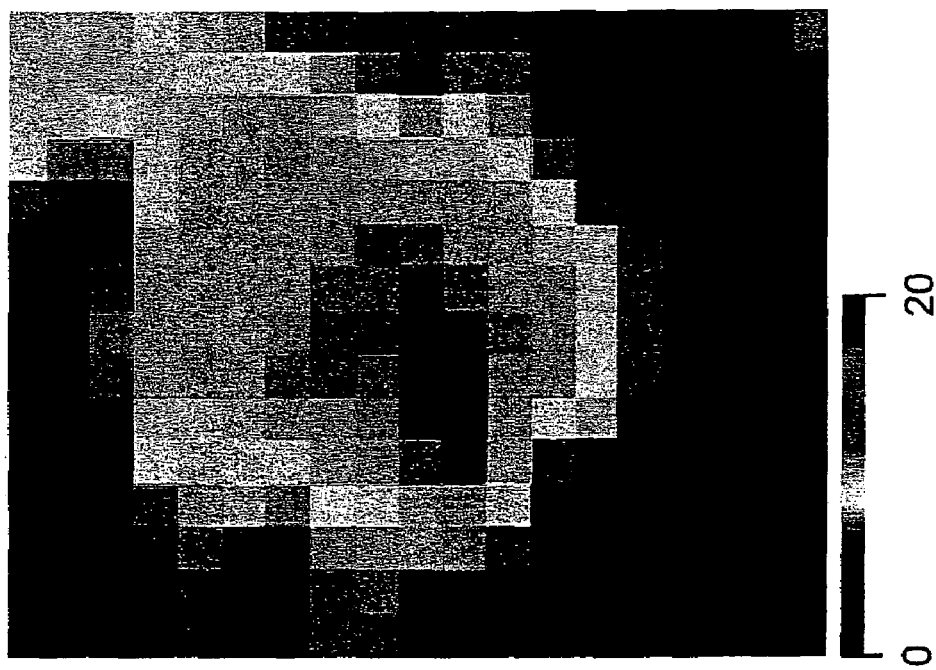

Diuretics: Kinetics effects: Non-invasive $^{23}$Na MRI enabled monitoring changes in renal sodium distribution in the rat induced by two different diuretic agents: furosemide, a loop diuretic, and mannitol, an osmotic diuretic. In these experiments, a high temporal resolution of 2–4 min was achieved that enabled characterizing the unique effect of each diuretic agent over time. Typical renal images recorded at this temporal resolution, both prior to and 8 minutes after the injection of 10 mg/kg body wt of furosemide, are presented in FIGS. 3A and 3B.

Figure 4A:
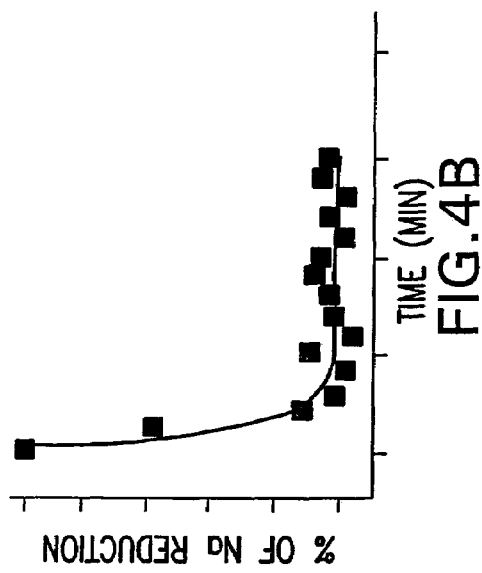
FIGS. 4A, 4B, 4C and 4D show typical dynamics of the change in the sodium distribution during diuresis. Data were obtained by an ROI-based analysis of sequential sodium images recorded before and after bolus injection of the diuretic agents at a time resolution of 2–4 min as described hereinafter in Materials and Methods.
Figure 4B:
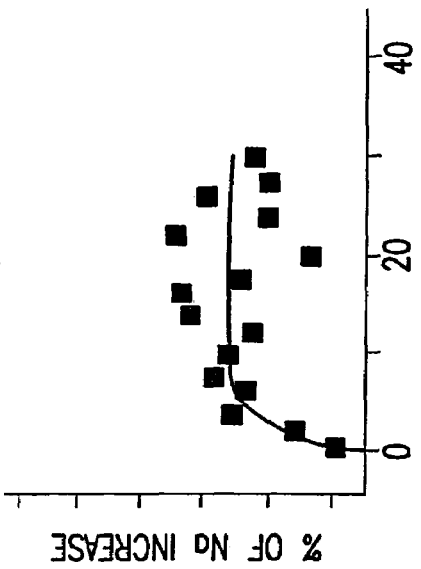

Despite the relatively lower signal-to-noise ratio in the images recorded at this temporal resolution, it was possible to determine the intensity of the sodium signal in the various regions of the kidney. After injection of furosemide or of mannitol the sodium concentration in the inner medulla decreased exponentially, in both instances, reaching a new "steady state" level [diuresis steady state $Na(t_s)$] but with different kinetics (FIGS. 4A and 4B, respectively). The decay of sodium content in the inner medulla relative to pre-treatment (expressed in percentages) appeared to behave according to the following equation, with a characteristic exponential decay time constant τ

$$Na(t) = Na(t_s) + [Na(t_0) - Na(t_s)] \times \exp\left(-\frac{t}{\tau}\right) \quad [1]$$

The time courses of the sodium decay were fitted to Equation 1, yielding a characteristic time constant of 2.5±0.4 min for mannitol, and 6.1±0.8 min for furosemide, with a decrease in sodium level of 52±5% (n=7) and 44±6% (n=7), respectively. Thus, mannitol reduced the sodium concentration in the inner medulla at a rate that was more than twofold faster than furosemide (p=0.002), however, the overall effect on the inner medulla was the same with either diuretics.

Figure 4C:
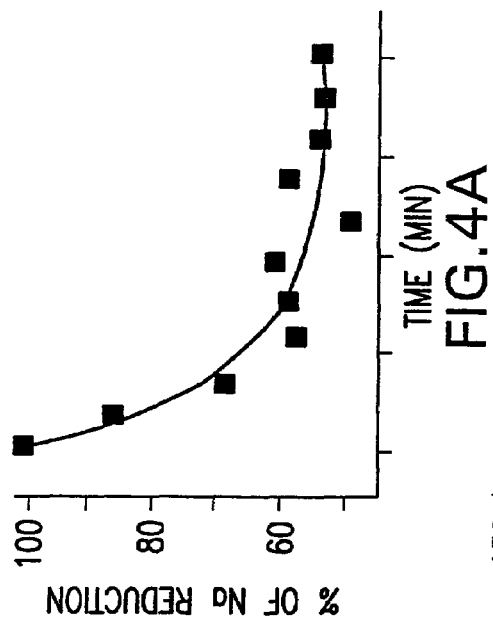
Figure 4D:
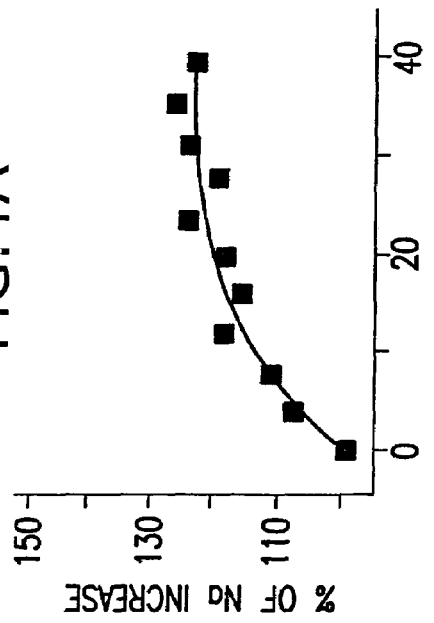

In the cortex, the high temporal resolution images generated a sodium signal-to-noise ratio that was low. Following treatment with furosemide or with mannitol, however, the signal intensity increased to measurable levels (FIGS. 4C and 4D, respectively). The increase was fitted to an equation similar to Equation 1, but with an exponential coefficient $[Na(t_s)-Na(t_0)]$. A consistently good fit (r=0.91) was obtained for furosemide, with a characteristic time constant of 9±1 min$^{-1}$ and 27±1% describing the total increase in sodium concentration (n=5). The data points obtained during mannitol treatment were too scattered to apply a "best fit" algorithm but indicated a general trend of about 25% increase in sodium concentration over time (FIG. 4D).

Diuresis steady state—An accurate characterization of the changes in the corticomedullary sodium gradient during "steady state" diuresis was obtained by recording images for 20–40 minutes using high spatial resolution as described in Materials and Methods, supra. Based on the results obtained in the dynamic studies (FIGS. 4A to 4D), images were recorded starting 15 minutes after administration of the diuretic agents. In three rats, a second post-injection image was subsequently recorded to confirm the "diuresis steady state". Indeed, no significant differences were observed in intensity distribution between the first and second post-injection images. This finding was as predicted from half-life time plasma levels, and from the reported long-term effects of furosemide and mannitol, Atherton J C, Hai M A and Thomas S. The time course of changes in renal tissue composition during mannitol diuresis in the rat. *J. Physiol.* 197: 411–428, 1968; and Brater D C. Clinical pharmacology of loop diuretics. *Drugs* 41: 14–22, 1991. Also examined was the effect of a 1 ml saline injection (maximum volume used) that served as a vehicle for administering the drugs. This amount of saline neither induced diuretic conditions, nor affected the sodium gradient (n=6).

Figure 5A:
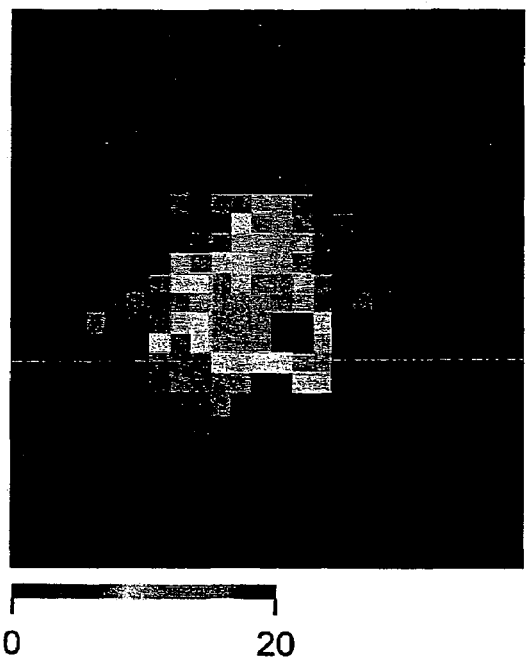
FIGS. 5A, 5B and 5C show renal sodium distribution under conditions of furosemide-induced diuresis steady state. Typical coronal $^{23}$Na MR images of the kidney were recorded before, FIG. 5A, and 15 min after, FIG. 5B, a bolus injection of furosemide (10 mg/kg body wt). Images were recorded using a 3D gradient echo sequence with TE/TR of 3.1/60 ms, spatial resolution of 0.974×0.974×5 mm and 40 min scanning time.
Figure 5B:
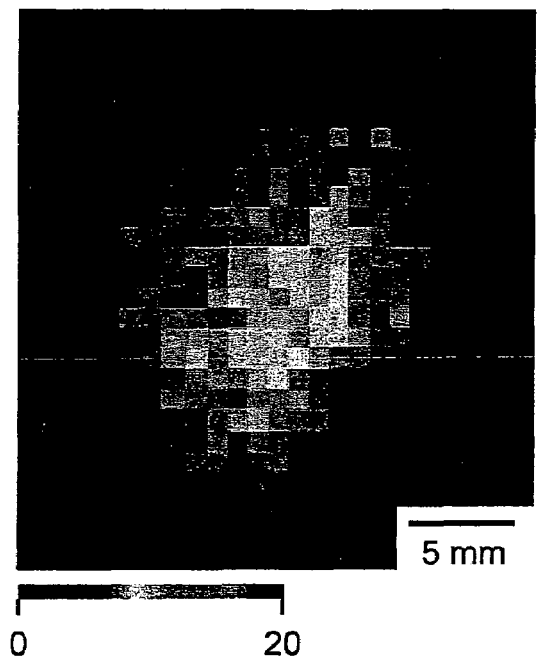
Figure 5C:
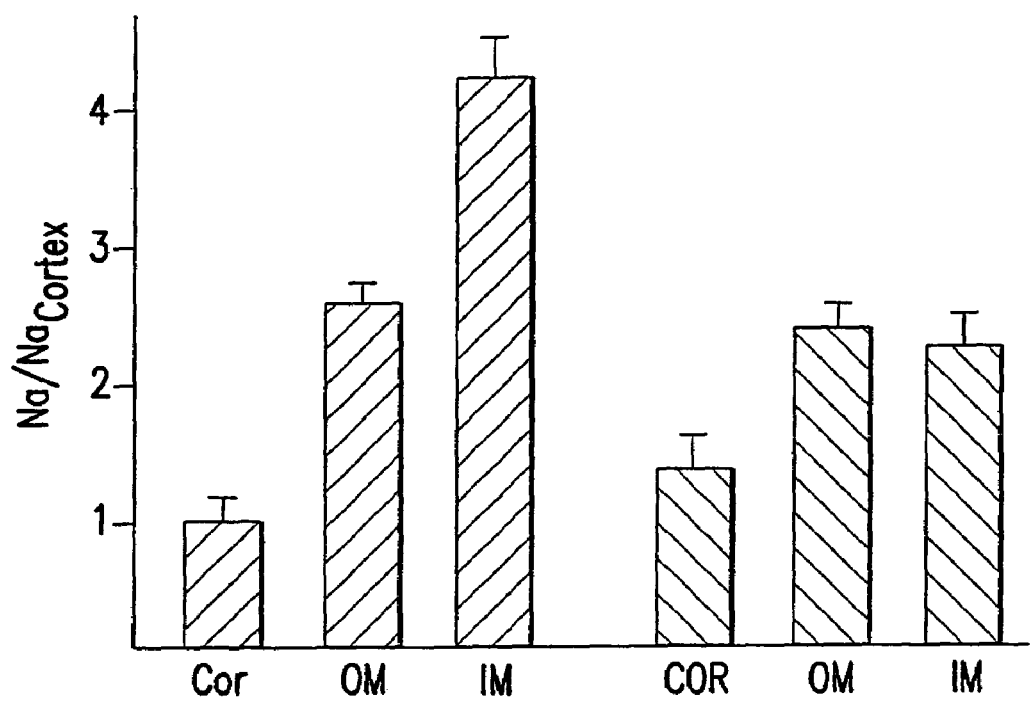

In "steady state" diuresis induced by furosemide (10 mg/kg body wt), the corticomedullary sodium gradient was almost completely cancelled (FIGS. 5A to 5C). The average sodium signal intensity in the inner and the outer medulla decreased by 47±5% (p<0.001) and 6±2% and (p<0.08) respectively (n=7), while that in the cortex increased by 25%±3% (p<0.001, n=7). Consequently, the highest levels of sodium concentration were found in the outer medulla; in the inner medulla, sodium concentration was slightly lower. The decrease in sodium signal intensity seen in the inner medulla was dose-dependent: after injecting separate animals with 10, 7 and 1 mg/kg body weight furosemide, the extent of decrease varied from 47±5% (n=7) to 40±4% (n=4) and 10±2% (n=3), respectively.

Figure 6A:
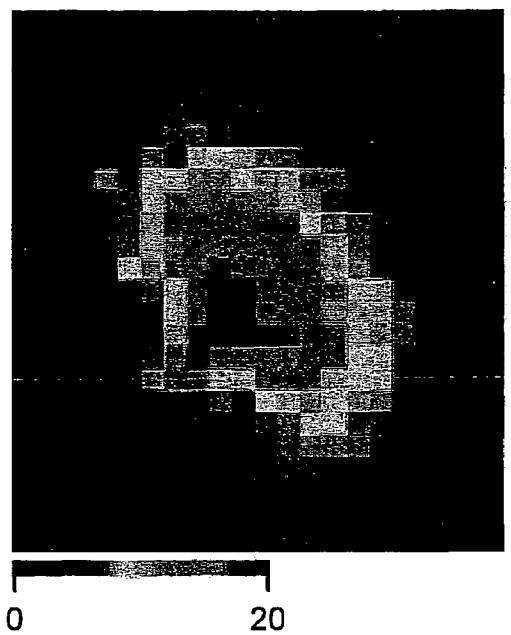
FIGS. 6A, 6B and 6C show renal sodium distribution under conditions of mannitol-induced diuresis steady state. Typical coronal $^{23}$Na MR images of the kidney recorded before, FIG. 6A, and 15 min after, FIG. 6B, a bolus injection of mannitol (20%, 1 ml). Images were recorded using a 3D gradient echo sequence with TE/TR of 3.1/60 ms, spatial resolution of 0.974×0.974×5 mm and 20 min scanning time.
Figure 6B:
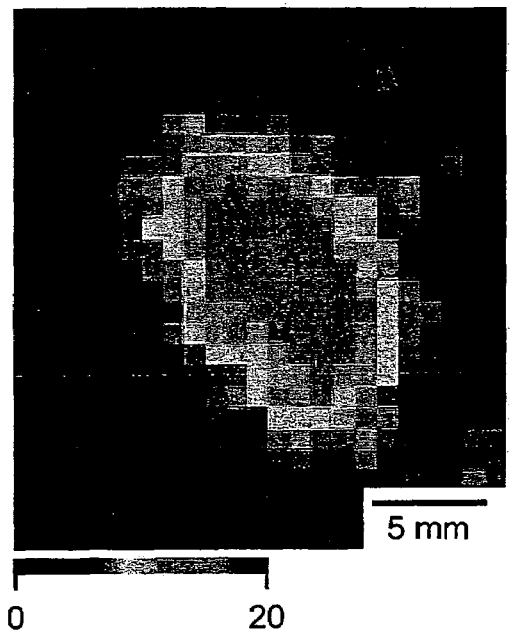
Figure 6C:
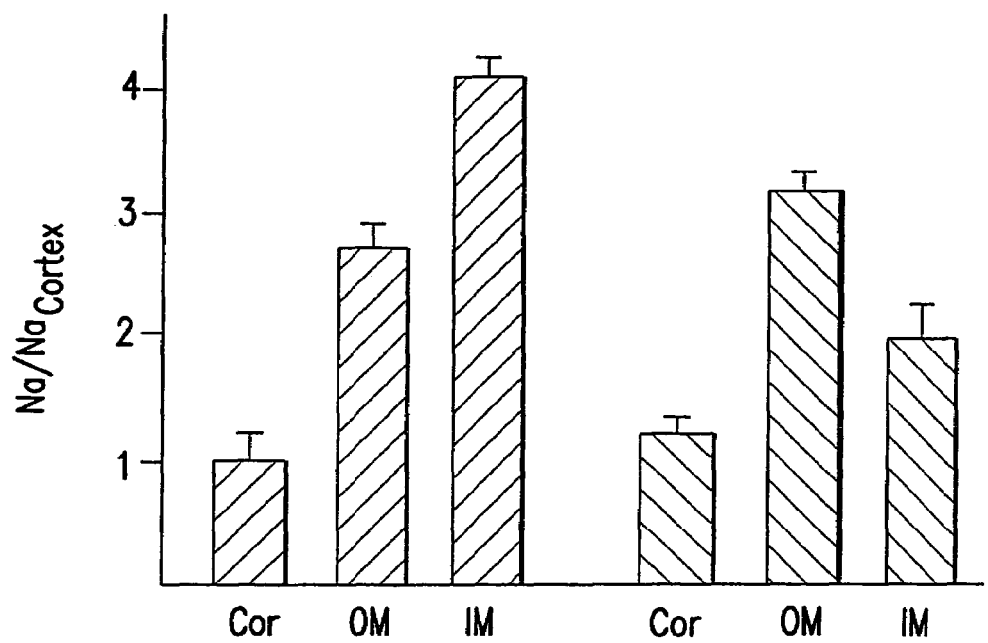

The effect of mannitol (1 ml, 0.1N) on sodium concentration in the inner medulla was similar to that of furosemide, inducing a decrease of 52±1% (p<0.001) and consequently leading to a marked breakdown of the corticomedullary sodium gradient (FIGS. 6A to 6C). Unlike the effects of furosemide, however, the cortico-outer medullar sodium gradient remained similar to that seen in control kidney following injection of mannitol. Moreover, the sodium signal intensity in the cortex increased by 20±2% (p<0.007), while that in the outer medulla increased by 13±1%, (p<0.02, n=7).

Figure 7A:
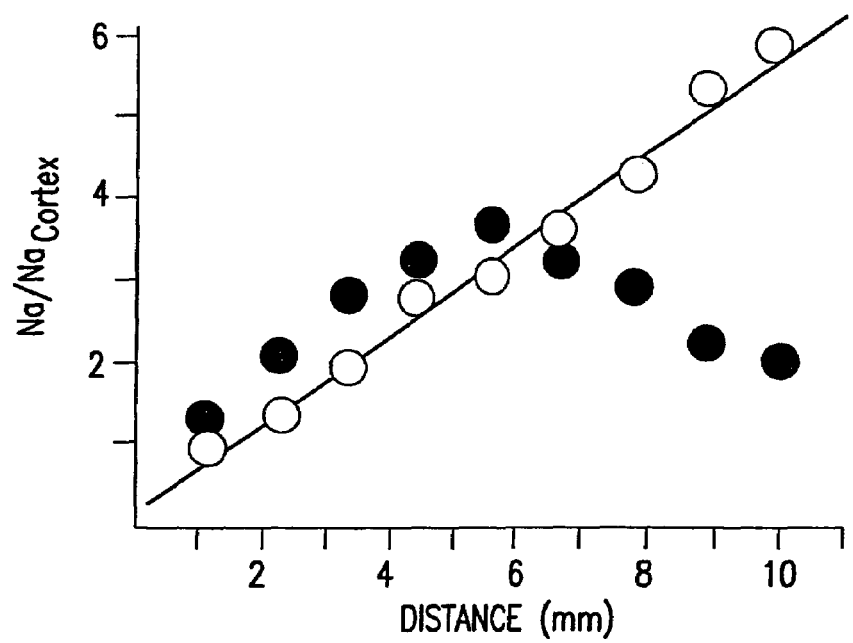
FIGS. 7A and B show modulation in the sodium distribution along the corticomedullary axis induced by diuretic agents.
Figure 7B:
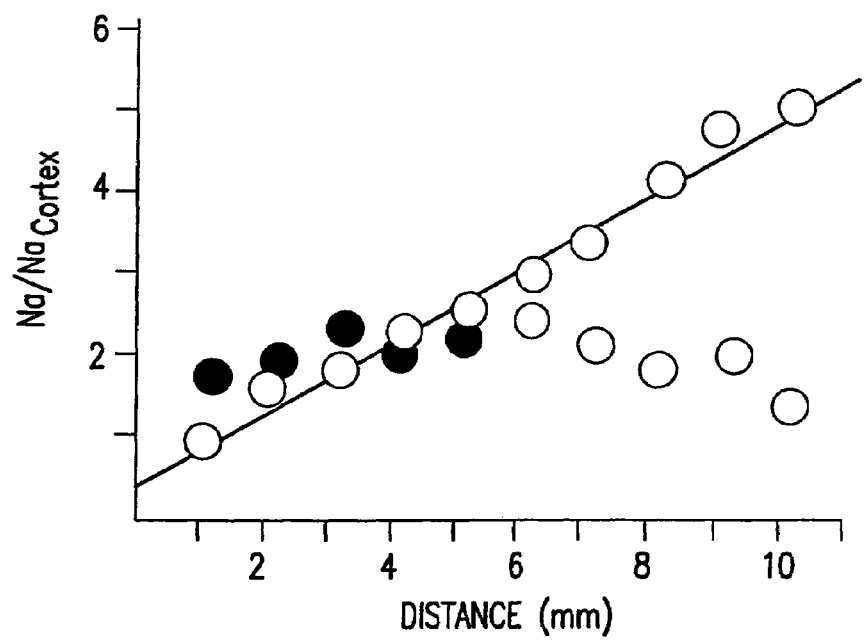

Sodium distributions under "steady state" diuresis induced by the two diuretic agents were far more clearly differentiated by analyzing the changes in the corticomedullary sodium gradient pixel-by-pixel (FIGS. 7A and 7B). Before diuretic treatment, the slope representing the sodium gradient along this axis was constant, as described above. Following treatment with each diuretic, the sodium concentrations along this axis exhibited two opposite slopes, a positive one from the cortex to the outer medulla, and a negative one from the outer to the inner medulla.

However, the extent of the new slopes was markedly different, depending on which diuretic was injected (p<0.001). If mannitol was used, the cortical-outer medullar gradient of 0.45±0.12 a.u.×mm$^{-1}$ (n=7) remained similar to the pretreatment gradient of 0.51±0.08 a.u.×mm$^{-1}$ (n=7). In contrast, furosemide diuresis caused a marked reduction in this slope, from 0.49±0.06 to 0.10±0.01 a.u.×mm$^{-1}$ (n=7). Consequently, as the sodium concentration at the papilla tip decreased by a similar extent after both treatments at steady state, the absolute values of the negative outer medulla-inner medulla gradient followed the same trend.

Figure 8:
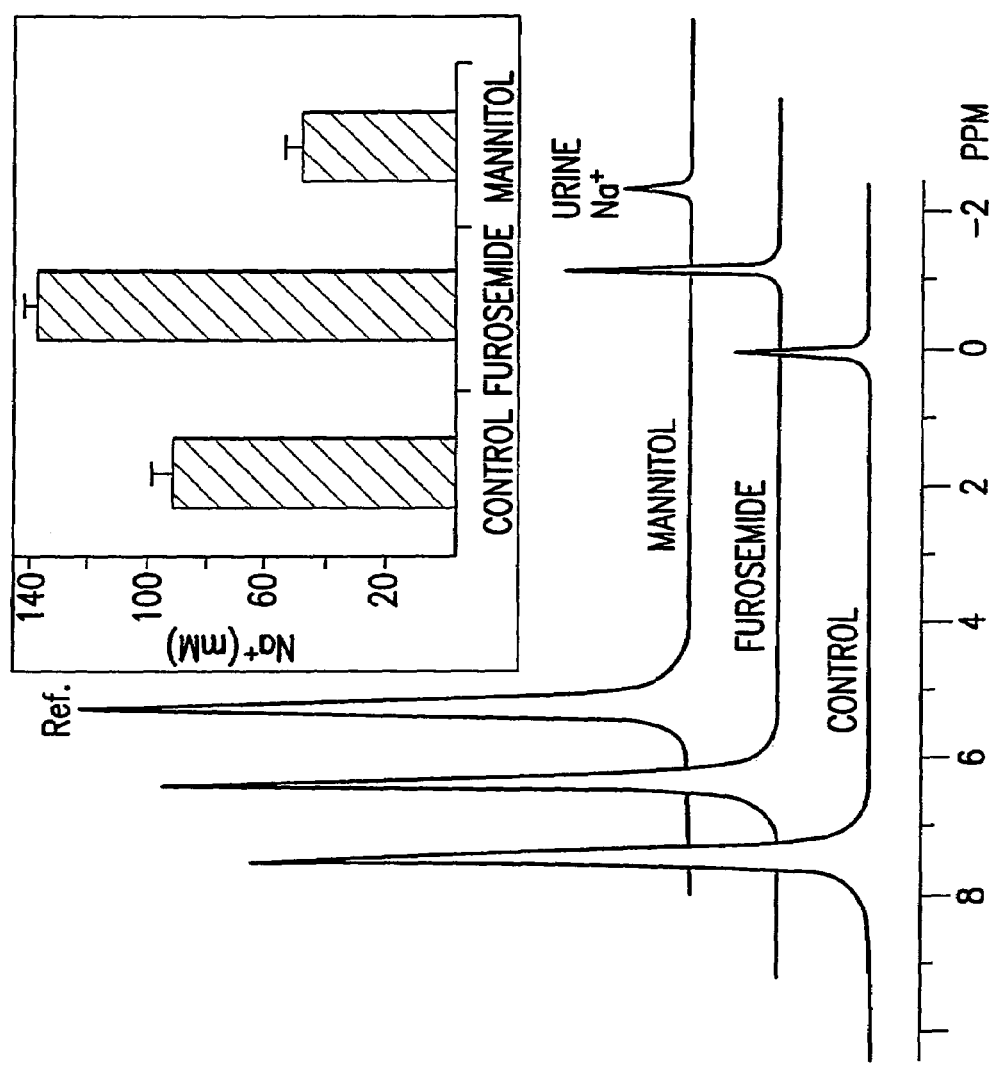
FIG. 8 shows changes in urine sodium concentration induced by furosemide and mannitol. $^{23}$Na spectra of urine samples recorded as described hereinafter demonstrate signals of the urine sodium (0 ppm) relative to a reference (150 mM shifter to ~7.5 ppm by TmDOTP$^{5-}$ as described hereinafter; the inset showing sodium concentration in the urine calculated from the integrated area of the urine sodium signal.

Effect of diuresis on urine sodium: A $^{23}$Na NMR spectroscopy was further utilized to determine changes in urine sodium concentrations induced by the two diuretics. A solution containing 150 mM Na$^+$ and the sodium shift reagent TmDOTP$^{5-}$ served as a concentration reference. Analyses of the urine sodium spectra (FIG. 8) showed that in the presence of furosemide, the urine sodium concentration increased by 50±5%, compared to the control (n=3), while in the presence of mannitol, it decreased by 49±3%, compared to the control (n=3). Thus, although both furosemide and mannitol reduced the amount of sodium in the inner medulla (FIGS. 4–7), these drugs, as expected, induced opposite effects on the total concentration of sodium in urine.

Sodium visibility during diuresis: The differences in sodium distribution during diuresis, as seen in the sodium images, could result from changes in the sodium content and/or from changes in the MR visibility of the sodium nuclei resulting from a marked alteration in the sodium microenvironment. Estimation of that visibility was obtained by $^{23}$Na spectroscopy that enabled detection of the slow and the fast relaxing components of the signal, thereby assuring 100% visibility (see Materials and Methods, supra). "Best-fit" analysis of the line shape of the sodium signal demonstrated the presence of two Lorenzian peaks at the same frequency, but with a different line width. The two transverse relaxation times ($T_2$) calculated from the width of the peaks at half height were found to be 11.5±3 ms and 2.1±0.5 ms, with a relative contribution to the total signal of 45±6% and 55±8%, respectively. Under furosemide diuresis (10 mg/kg body wt), no difference was found neither in the integrated area of the signal nor in the relaxation times (n=3). This implied that the diuresis-induced changes documented in the sodium images predominantly reflected changes in sodium concentration, rather than changes in the visibility of the sodium nuclei.

Discussion—The foregoing demonstrated the ability of 3D $^{23}$Na magnetic resonance imaging to detect, in vivo, the detailed spatial distribution of sodium in the intact rat kidney. By mapping renal sodium distribution non-invasively and at high resolution, changes in this distribution could be related to specific physiological mechanisms: the loop diuretic mechanism of furosemide, and the osmotic diuretic mechanism of mannitol.

The MR sensitivity of the sodium ($^{23}$Na) nucleus is ~3 orders of magnitude lower than that of proton ($^1$H). Moreover, the concentration of sodium in tissues is ~2 orders of magnitude lower than that of protons. Therefore, in vivo $^{23}$Na MR images exhibit a signal-to-noise ratio that is ~2 orders of magnitude lower than that of in vivo $^1$H MR images. Nevertheless, the extensive extracellular volume of the kidney, including the intravascular and the intraluminal spaces, as well as, the marked increase of sodium content due to the countercurrent mechanism enabled selective imaging of the renal sodium at a planar spatial resolution of less than 1 mm$^2$. With this fine resolution, one was able to observe in great detail the changes in sodium concentration in the various parts of the kidney.

In general, the renal cortex is mostly composed of glomeruli, proximal and distal tubules, and the beginning of the collecting duct, Lote C J. *Principle of renal physiology.* London: Chapman&Hall, 1994. The fluid in the proximal tubule was shown to be isotonic with the plasma, Windhager E E and Giebisch G. Micropuncture study of renal tubular transfer of sodium chloride in the rat. *Am J. Physiol.* 200: 581–590, 1961; and Roy D R and Jamison R L. Countercurrent system and its regulation. In: *The kidney: physiology and pathophysiolog.*, edited by Seldin D W and Giebrisch G. New York: Raven Press, 1985, p. 903–932, indicating that the filtration of the plasma in the glomerulus, and the reabsorption of the filtrate from the proximal convoluted tubules, do not affect the sodium concentration in the nearby interstitium. Although the cortical distal tubule fluid is hypotonic relative to plasma, due to the extensive reabsorption of sodium from the thick ascending limb, tissue slice studies revealed that the sodium concentration in the cortex is similar to that of the plasma [Jamison R L and Kriz W. *Urinary concentrating Mechanism.* New York Oxford: Oxford University Press, Inc., 1982, and references cited therein]. Therefore, it was reasonable to infer that the sodium concentration in the cortex is equal to that in the plasma.

The sodium images of the kidney revealed low signal intensity in its outermost region: this would be expected for the cortex, which has the lowest sodium concentration of all the regions of the kidney. Previous studies of the exposed rabbit kidney have also demonstrated in the cortex a low sodium signal that was close to the noise level, but which increased after saline infusion, Wolff S D, Eng J, Berkowitz B A, James S and Balaban R S. Sodium-23 nuclear magnetic resonance imaging of the rabbit kidney in vivo. *Am. J. Physiol.* 258: F1125–F1131, 1990; and Bansal N and Seshan V. Three-dimensional triple quantum filtered 23-Na imaging of rabbit kidney with weighted signal averaging. *J. Magn. Reson. Imag.* 5: 761–767, 1995.

The MR images clearly revealed increased levels of sodium in the outer and inner medulla relative to the cortex, as is well known. According to the ROI based analysis the inner medulla to cortex sodium concentration ratio is 4:1. A higher ratio of 6:1 was found using the pixel-by-pixel analysis. These differences resulted from the vast averaging required by the ROI based analysis, and emphasize the advantage of the second analysis, and the necessity of high resolution imaging to assess accurately the corticomedullary sodium gradient. Most significantly, pixel-by-pixel analysis indicated the presence of a linear rather than an exponential increase along the corticomedullary axis. A very recent study, Edwards A, Delong M J and Pallone T L. Interstitial water and solute recovery by inner medullary vasa recta. *Am. J. Physiol. Renal Physiol.* 278: F257–F269, 2000, predicted that the sodium concentration would increase exponentially in the inner medulla, as was observed by Koepsell et al, Koepsell H, Nicholson W A P, Kriz W and Hohling H J. Measurements of exponential gradients of sodium and chlorine in the rat kidney medulla using electron microprobe. *Pflugers Arch.* 350: 167–184, 1974, by means of an electron microprobe technique. However, in the latter, Koepsell et al study, the exponential increase led to twelve-fold higher sodium concentration in the papilla compare to that in the cortex. This value is much higher than the value of ~6 that was obtained from the pixel-by-pixel analysis (FIGS. 2A and 2B). Moreover, the inner medulla-to-cortex sodium concentration ratio of ~4:1 obtained from the ROI-based analysis is well within the range of values (2.5–5) reported previously, Azar S, Tobian L and Ishii M. Prolonged water diuresis affecting solutes and interstitial cells of renal papilla. *Am. J. Physiol.* 221: 75–79, 1971; Bengele H H, Mathias R S, Perkins J H and Alexander E A. Urinary concentrating defect in aged rat. *Am. J. Physiol.* 240: F147–F150, 1981; Buerkert J, Martin D, Prasad J and Trigg D. Role of deep nephrons and the terminal collecting duct in mannitol-induced diuresis. *Am. J. Physiol.* 240: F411–F422, 1981; Gennari F J, Johns C, Caflisch C R and Cortell S. Dissociation of saline-induced natiuresis from urea washout in the rat. *Am. J. Physiol.* 241: F250–F256, 1981; Jamison R L. The renal concentrating mechanism: micropuncture studies of the renal medulla. *Fed. Proc.* 42: 2392–2397, 1983; Martinez-Maldonado M, Eknoyan G and Suki W N. Influence of volume expansion on renal diluting capacity in the rat. *Clin. Sci. Mol. Med.* 46: 331–345, 1974; Pallone T L, Yagil Y and Jamison R L. Effect of small-solute gradients on transcapillary fluid movement in renal inner medulla. *Am. J. Physiol.* 257: F547–F553, 1989; Valtin H. Sequensuration of urea and non urea solutes in renal tissues of rats with hereditary hypothalamic diabetes insipidus: effect of vasopressin and dehydration on countercurrent mechanism. *J. Clin. Invest.* 45: 337–345, 1966; and Wolff S D, Eng J, Berkowitz B A, James S and Balaban R S. Sodium-23 nuclear magnetic resonance imaging of the rabbit kidney in vivo. *Am. J. Physiol.* 258: F1125–F1131, 1990. Thus, the results, obtained with a direct imaging method of the present invention, suggest that the countercurrent multiplier mechanism induces a linear corticomedullary sodium gradient in the rat kidney.

Although furosemide and mannitol act in different ways, the sodium concentration in the inner medulla reached similar level 15 min after injection of either diuretic. It was therefore necessary to significantly decrease the imaging time, in order to monitor more precisely the dynamic changes resulting from the influence of these two diuretics. Reducing this time by tenfold yielded a temporal resolution of 2–4 minutes that enabled efficient monitoring of the time course of diuresis, even though there was a giving up of about 40% of the voxel resolution. With this low resolution only the cortex and the inner medulla sodium could be accurately detected.

Thus, it was possible to determine that the dynamic effect of the diuretics on the sodium concentration in the inner medulla followed a mono-exponential decay, with mannitol causing a twofold faster decay, compared to furosemide. This nature of the decay suggests that the countercurrent mechanism was fully inhibited; consequently, the rate of decay was proportional to the difference in sodium concentration between the inner medulla and the cortex. The slower decay rate caused by furosemide may reflect the time it takes for this drug to reach its site of action. This is in accordance with the finding that the amount of furosemide reaching the renal tubule, rather than the quantity present in the plasma, determines the extent of its diuretic effect, Boles Ponto L L and Schoenwald R D. Furosemide (frusemide) a pharmacokinetic/pharmacodynamic review (part 1). *Clin. Pharmacokinet.* 18: 381–408, 1990.

Furthermore, it was found that at "diuretic steady states" two main effects were induced in the kidney, a major effect in the inner medulla, and a minor effect in the outer medulla. In the inner medulla, diuresis results in a decrease of ~50% in sodium concentration. Similar observations of the redistribution of sodium following diuretic injection, and of a marked decrease of sodium in the inner medulla, were reported, though invasive rather than non-invasive techniques were used, Buerkert J, Martin D, Prasad J and Trigg D. Role of deep nephrons and the terminal collecting duct in mannitol-induced diuresis. *Am. J. Physiol.* 240: F411–F422, 1981; Pallone T L, Yagil Y and Jamison R L. Effect of small-solute gradients on transcapillary fluid movement in renal inner medulla. *Am. J. Physiol.* 257: F547–F553, 1989; Atherton J C, Hai M A and Thomas S. The time course of changes in renal tissue composition during mannitol diuresis in the rat. *J. Physiol.* 197: 411–428, 1968; Lang F. Osmotic diuresis. *Renal Physiol.* 10: 160–173, 1987; Wilson D R and Sonnenberg H. Urea secretion in medullary collecting duct of the rat kidney during water and mannitol diuresis. *Am. J. Physiol.* 240: F165–F171, 1981. As this is a marked, noticeable decrease, its detection does not require high-quality imaging or pixel-by-pixel analysis. However, this effect is non-specific, and is observed when diuresis is induced with either furosemide or mannitol.

In contrast, the effect of these diuretic agents on the outer medulla is specific. In the presence of mannitol, an osmotic diuretic, the sodium concentration increased compared to control, whereas in the presence of furosemide, a loop diuretic, the sodium concentration decreased compared to control.

Due to the fact that in control kidney, the sodium concentration in the outer medulla is much lower than that in the inner medulla, the changes seen under diuretic conditions are much smaller than those observed in the inner medulla. Consequently, in order to detect changes in sodium concentration in the outer medulla, the image quality (resolution and signal-to-noise ratio) must of necessity be high. Moreover, the averaging of values, a necessary precondition for a ROI based analysis, makes it impossible to clearly detect the specific changes in the outer medulla under such conditions. Therefore, in accordance with the present invention, it is necessary to undertake a pixel-by-pixel MRI analysis of sodium concentration along the corticomedullary axis; such action yielded a sodium gradient, which could be clearly expressed in terms of a linear slope. This analysis enabled detection and description of the changes in sodium concentration in the outer medulla in great detail, and with a significantly higher level of accuracy.

Thus, as the highest concentrations of sodium, during diuresis, were found in the outer medulla, the linear sodium gradient was measured from the cortex to the outer medulla. The extent of this gradient was fivefold higher in mannitol induced diuresis than in furosemide induced diuresis and, therefore, it reflected the differing mechanisms of action of these two diuretics. Furosemide acts on the outer medulla, where it prevents sodium reabsorption into the interstituim add thereby reduces the sodium concentration in this region. This decrease was not observed when mannitol was injected, since this agent mainly acts on the inner medulla rather than on the outer medulla. In this latter instance, the reabsoption of sodium, which is only moderately affected by mannitol, together with the sodium washout from the inner medulla, elevates the levels of sodium in the outer medulla.

Unlike the reduction in sodium concentration in the inner medulla, furosemide and mannitol exerted opposite effects on sodium concentration in the urine. Similar results were previously observed by other methods, Buerkert J, Martin D, Prasad J and Trigg D. Role of deep nephrons and the terminal collecting duct in mannitol-induced diuresis. *Am. J. Physiol.* 240: F411–F422, 1981; Pallone T L, Yagil Y and Jamison R L. Effect of small-solute gradients on transcapillary fluid movement in renal inner medulla. *Am. J. Physiol.* 257: F547–F553, 1989; Ellison D H, Velazquez H and Wright F S. Adaptation of the distal convoluted tubule of the rat; structural and functional effects of dietary salt intake and chronic diuretic infusion. *J. Clin. Invest.* 83: 113–126, 1989; and Szenasi G, Bencsath P and Takacs L. Proximal tubular transport and urinary excretion of sodium after renal denervation in sodium depleted rats. *Pflugers Arch.* 403: 146–150, 1985). The reduction in the sodium concentration in the inner medulla during diuresis could be due to changes in sodium concentration in the interstitial fluid and in the collecting duct filtrate in this region. The latter has solute composition similar to that of the urine. The fact that furosemide and mannitol exerted opposite effects on the urine indicates that most of the recorded sodium signal in the images is due to the sodium content in the interstitium. Furthermore, increased levels of sodium in the urine following furosemide treatment could be correlated with the decrease in sodium in the outer medulla, as both effects stem from inhibition of sodium reabsorption in the thick ascending limbs. As mannitol only moderately affects the reabsorption of sodium in the outer medulla, the sodium concentration in the urine decreased compared to control, due to its marked osmotic effect.

Summarizing, by the present invention it has been possible to characterize in detail, in an in vivo model of the rat kidney, the corticomedullary sodium gradient and its specific modulation as induced by two different diuretic agents, which was found to be linear in nature. The ability to utilize non-invasive magnetic resonance imaging to describe the renal sodium gradient in unprecedented detail by means of a pixel-by-pixel analysis of the slope of the sodium concentration along the corticomedullary axis, according to the practice of the present invention, provides a quantitative, reproducible tool to assess kidney function, and is of great value in the clinical setting.

Turning now to another aspect of the present invention, the following disclosure is with reference to FIGS. 9 to 13 and concerns in vivo $^{23}$Na MRI studies of the spontaneous- and experimental acute hydronephrosis of the rat kidney. By the present invention, detailed evaluation of the sodium concentration along the corticomedullary axis was correlated with histological findings. The results show the capacity of this non-invasive tool of the present invention to characterize the extent of obstruction and the residual function of the kidney in a quantitative manner.

Materials and Methods: Animals: Female adult Lewis rats weighting 250–300 g had free access to a standard diet and water throughout the entire experimental period. In all studies the rats were anesthetized by an intraperitoneal injection of sodium pentobarbital at a dose of 0.04 mg/g wt. All animal protocols and maintenance were in accord with the guidelines of the Committee on Animals of the Weizmann Institute of Science and were approved by this committee.

Experimental hydronephrosis: The rats were anesthetized and then the left kidney was exposed by a flank incision, and the ureter was ligated near the pelvic-ureter junction with a double 5/0 silk suture.

Creatinine level in the plasma was measured in blood samples, each of ~1 ml, that were drawn from each rat and collected in a tube containing 100 μl heparine (Elkins-Sinn, Inc., New Jersey). Following centrifugation at room temperature for 10 min (10,000 g) the supernatant was separated and creatinine level was determined using a standard creatinine kit (Signa Diagnostics, Inc., St. Louis) by a spectrophotometric measurement at 500 nm (Spectronic 1001, Bausch & Lomb, USA). The hydronephrotic kidney was imaged two days after the surgery and then the rat was sacrificed and the kidney was dissected free and cut in the middle in the same plane as the recorded MR images. The two parts of the kidney were fixed in 4% formaldehyde solution and embedded in paraffin. Then, sections of 4-μm thickness were dissected and stained with hematoxylin-eosin for histology examination.

Diuresis: Furosemide (Hoechst, Germany) solution of 10 mg/ml was injected as a bolus into the rat-tail vein at a dose of 10 mg/kg wt.

In-vivo MRI: $^1$H and $^{23}$Na images and spectra were recorded at 200 and 53 MHz respectively with a 4.7 T Biospec spectrometer (Bruker, Karlsrhue, Germany) using a home built 3-cm, $^1$H and $^{23}$Na tuned surface coil. The rat was placed on the coil in a supine position with the kidney positioned in the middle of the coil. Axial and coronal 3D $^1$H gradient echo images were recorded for localization of the kidney using an echo time/repetition time (TE/TR) of 6/30 ms FOV of 12×12×3.2 cm and matrix of 256×256×32. 3D gradient echo $^{23}$Na images were recorded using (TE/TR) of 1.7/60 ms and a 90° OSIRREAD adiabatic pulse, field of view (FOV) of 12×12×8 mm, and matrix of 128×128×16, with 20 scans (40 min).

Figure 10A:
FIGS. 10A, 10B, 10C and 10D show gradient echo images (TE/TR/α: 6.5/27/45°) of a coronal central slice of the left kidney of a female Lewis rat before, FIG. 10A; 6 sec, FIG. 10B; 64 sec, FIG. 10C; and 70 min, FIG. 10D, after a bolus injection of 0.05 mmol/kg wt Gd-DTPA. Images were recorded with temporal resolution of 6 sec and spatial resolution of 0.34×0.34×1 mm.
Figure 10B:
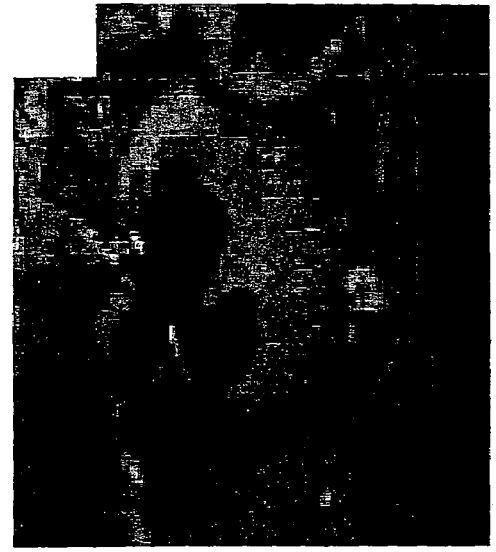
Figure 10C:
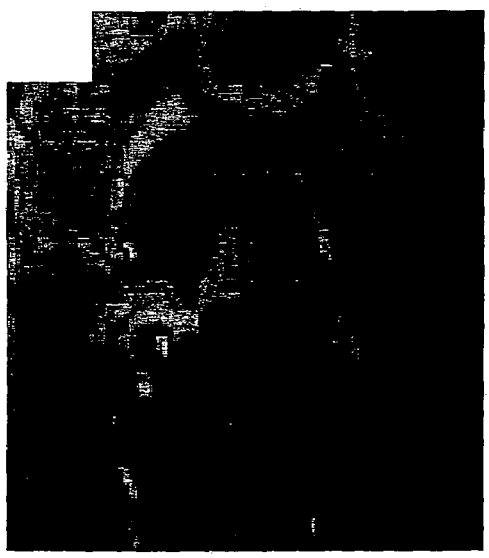

A Fermi filter was applied on the k-space before performing the Fourier transformation. The basic equation of the filter is:

$$f(x) = \frac{1}{1 + \exp\left(\frac{\mathrm{abs}(x - \mathrm{matrix\_size}) - a}{b}\right)} \quad [1]$$

where the matrix size of the $^{23}$Na images was 128, and a and b are adjustable free parameters of the filtering process. The optimized values of a and b in the experimental set up were 50 and 20, respectively. This function was applied on a 2D grid, which had the same dimensions as the K-space of the sodium image. The resulting matrix was multiplied with each of the 16 K-space planes of the raw data (FIG. 10B). The 3D images were obtained by performing 3D Fourier transformation on the resulting filtered 3D K-space cube.

The MR visibility of the sodium nuclei in the kidney was evaluated in reference to a standard of a saline solution in a sealed plastic tube that was transplanted near the kidney of untreated rats and imaged as above.

The sodium image was analyzed by a pixel by pixel analysis that was performed in order to assess the behavior of the NMR sodium signal along the corticomedullary axis. In this analysis, the pixel intensities were measured along a defined line from the cortex to the inner medulla and were plotted versus the distance of the pixel from that of the cortex.

In the contrast enhanced studies a 40 mm $^1$H volume coil (Bruker) was used applying a 2D $^1$H-T1 weighted gradient echo sequence with TE/TR=6.5/27 and a pulse angle of 45° FOV of 12×12 cm, matrix of 256×256, 1 mm slice thickness and 1 scan. Consecutive images were recorded prior to and 6 seconds after the injection of Gd-DTPA (0.05 mM/Kg wt) to the tail vein with a temporal resolution of 6 seconds.

The results are presented as mean±SEM (standard error of the mean). Statistical analysis to evaluate differences between pixels in the same image was performed by paired student's t-test (2-tails). Otherwise unpaired student's t-test (2-tails) was used.

Figure 9A:
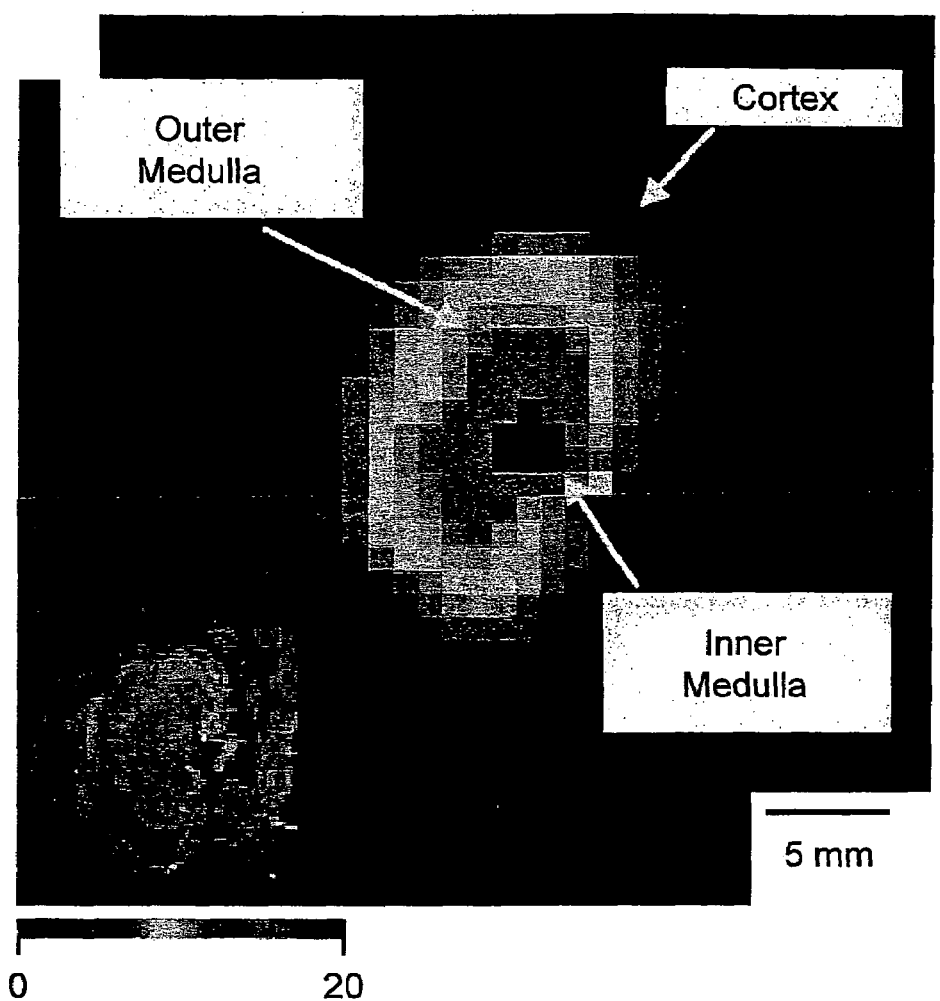
FIGS. 9A and 9B shows in FIG. 9A coronal $^{23}$Na image of the right kidney in a female Lewis rat. The image was recorded using a 3D gradient echo sequence with TE/TR of 1.7/60 ms, spatial resolution of 0.974×0.974×5 mm and 20 min scanning time. A fermi filter was applied on the row data before the Fourier transformation as described in Material and Methods.
Figure 9B:
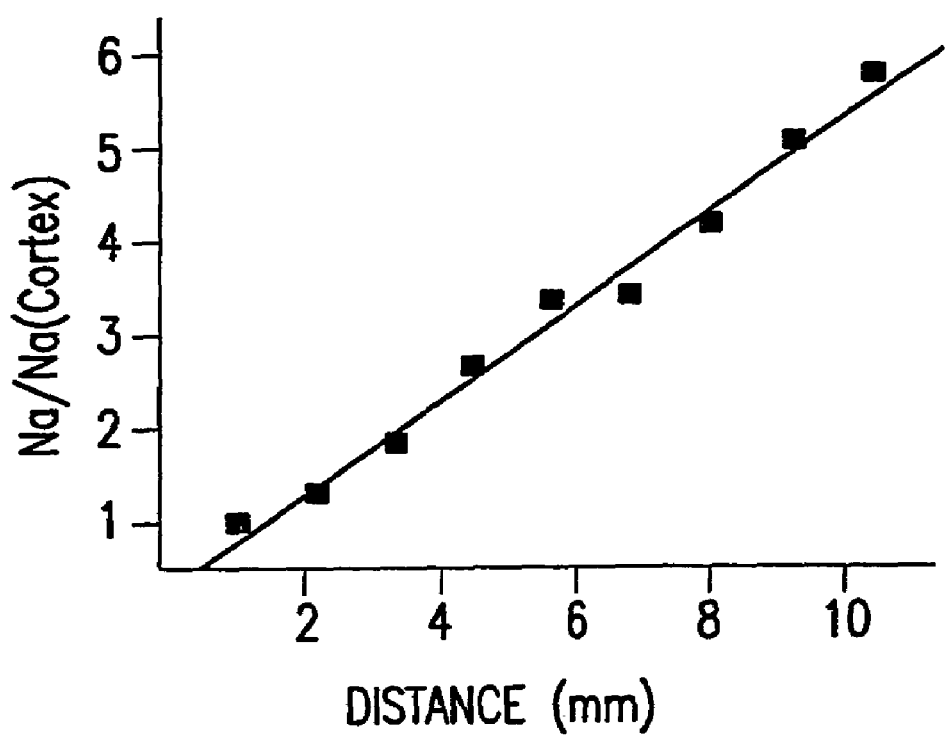

Results: The corticomedullary sodium gradient: Sodium images of the rat kidney revealed gradual changes in the signal intensity along the kidney from the cortex through the medulla, reaching the highest intensity in the inner medulla (FIGS. 9A and 9B). Pixel by pixel measurement along the corticomedullary axis showed a linear increase of the signal intensity with a slope of 0.51±0.07 a.u.×mm$^{-1}$ (R=0.97±0.01, n=17). Assuming that the concentration of sodium in the cortex is equal to that of the plasma, 145 mM (Jamison, R. L., and W. Kriz. *Urinary concentrating Mechanism*. New York Oxford: Oxford University Press, Inc., 1982 and references cited therein), a gradient of 74±10 mM×mm$^{-1}$ for the linear sodium increase along the corticomedullary axis was calculated (FIG. 9B). Sodium images were also recorded at varying TRs (50–400 ms) and TEs (6–1.7 ms), yielding consistently the same slope for the linear increase of the sodium. This also reconfirmed that the $T_1$ and $T_2$ relaxation times of $^{23}$Na are similar throughout the entire kidney as was previously reported, Wolff, S. D., J. Eng, B. A. Berkowitz, S. James, and R. S. Balaban. Sodium-23 nuclear magnetic resonance imaging of the rabbit kidney in vivo. *Am. J. Physiol.* 258: F1125–F1131, 1990. Thus, the differences observed in the renal sodium signal intensity are entirely due to the changes in sodium concentrations. The intensity of the MR sodium signal in tissues depends on the concentration and the visibility of this nuclei, Boulanger, Y., and P. Vinay. Nuclear magnetic resonance od sodium in biological tissues. *Can. J. Physiol. Pharmacol.* 67: 820–828, 1989. The visibility was determined in reference to a saline solution (100% visibility) implanted near the kidney. Analysis of the signal intensities of the cortex versus that of the saline solution, taking into account the different height from the surface coil and the in plane distance from the center of the coil indicated a visibility of 46±1% (n=3).

Spontaneous hydronephrosis: Two rats, eight-month- and one-year old, have developed spontaneously unilateral hydronephrosis as a result of ureter obstruction. $^1$H images showed dilation of the obstructed ureter compared to control, however no change was observed in the total size of the kidney compared to the normal kidney.

Figure 10D:
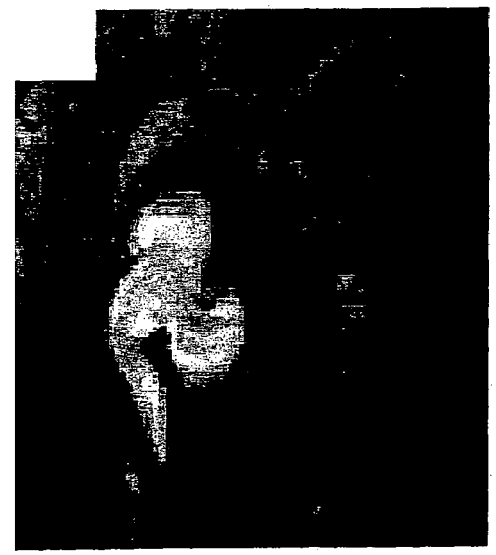

The presence of obstruction was detected by monitoring the kidney under diuresis with furosemide using the dynamic contrast enhanced protocol, as was previously reported, Rothpearl, A., D. Frager, A. Subramanian, B. Bashist, J. Baer, C. Kay, K. Cooke, and C. Raia. MR urography: technique and application. *Radiology* 194: 125–130, 1995. Immediately after the administration of the contrast agent the parenchyma was rapidly enhanced while the contrast agent could not enter the dilated ureter (FIG. 10A). Therefore, clear contrast was observed between these two regions (FIG. 10B). As expected, under diuresis no $T_2$ shortening effect and consequently darkening of the signal intensity were observed. Sixty four seconds after the administration of the contrast agent it entered rapidly to the renal pelvis and to the ureter (FIG. 10C), but was not cleared toward the ureter until the end of the experiment (75 minutes after the contrast agent administration), indicating the presence of complete obstruction (FIG. 10D).

Figure 11A:
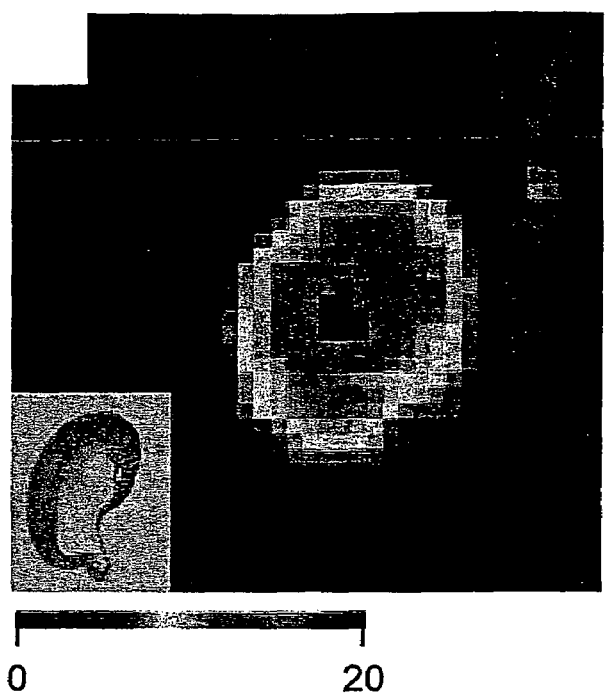
FIGS. 11A and 11B show renal sodium distribution under conditions of spontaneous, FIG. 11A, and acute experimental, FIG. 11B, hydronephrosis. Images were recorded using a 3D gradient echo sequence with TE/TR of 3.1/60 ms, spatial resolution of 0.974×0.974×5 mm and 20 min scanning time. Inset, are pictures of macro histology slices of the corresponded imaged kidneys showing the size of the residual parenchyma.
Figure 12A:
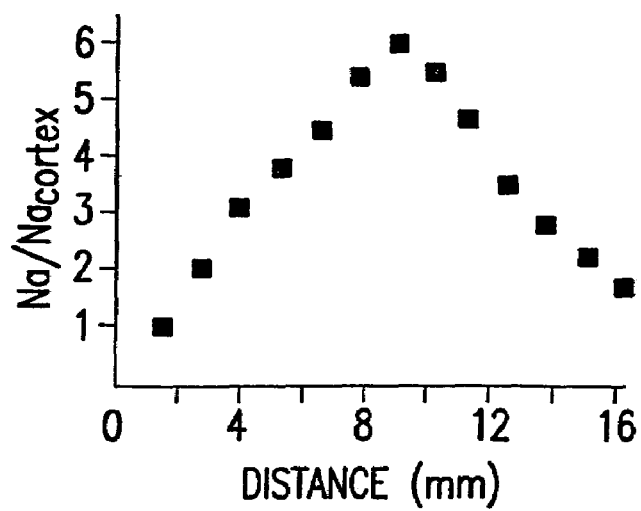
FIGS. 12A, 12B and 12C show modulation in the corticomedullary induced by spontaneous hydronephrosis, FIG. 12A, acute hydronephrosis, FIG. 12B, and furosemide, FIG. 12C. Sodium concentration relative to that in the cortex was measured using a pixel-by-pixel analysis of the sodium images as described hereinafter.

The same kidneys were imaged by $^{23}$Na MRI and expressed abnormal sodium distribution (FIG. 11A). The inner medulla did not exhibit the higher sodium signal intensity as in the normal kidney, but exhibited the same signal intensity as in the cortex. The highest sodium signal, threefold higher than that in the cortex, was confined to the outer medulla. Pixel by pixel analysis along the corticomedullary axis indicated a marked change in the sodium gradient from the outer medulla to the inner medulla (FIG. 12A). The extent of the cortico-outermedullar slope (0.60±0.02 a.u×mm$^{-1}$, n=2) was not significantly different from that in the control kidney.

Figure 13A:
Figure 13B:
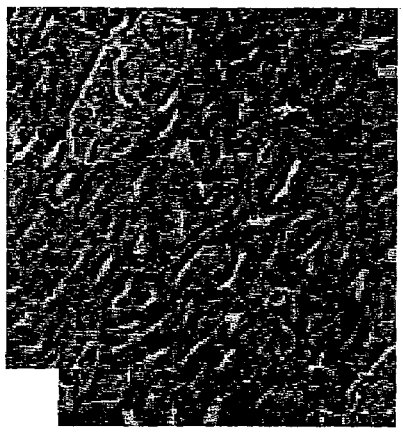
Figure 13C:
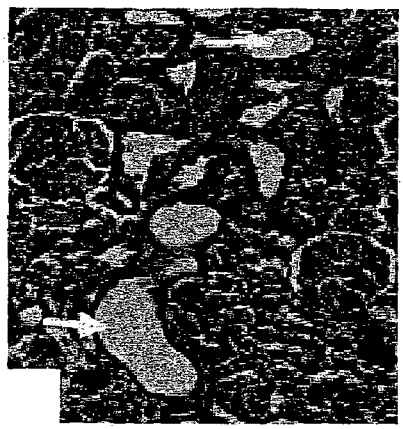
Figure 13D:
Figure 13E:
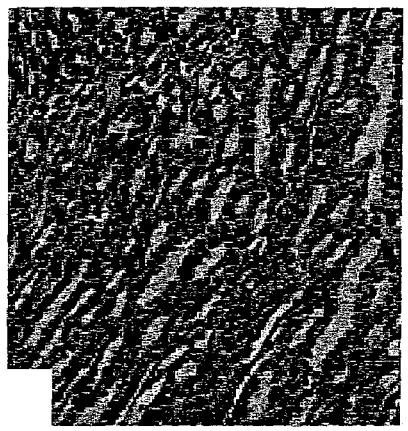

Macro inspection of the histological specimens of the obstructed kidneys confirmed hydronephrosis caused by ureter obstruction (FIG. 11A insert). A marked reduction in the parenchyma thickness was observed (~5 mm compared to ~12 mm in the right kidney) where the atrophy of the perihelia region was larger than that of the circumference. Despite this abnormal pattern, the structure and cellular morphology of the cortex appeared unharmed, with no glomerular or tubular stenosis, necrosis or atrophy. In addition, the remaining medullar cells did not show any significant signs of abnormalities (FIGS. 13E, 13H) compared to control (FIGS. 13D, 13G).

Figure 11B:
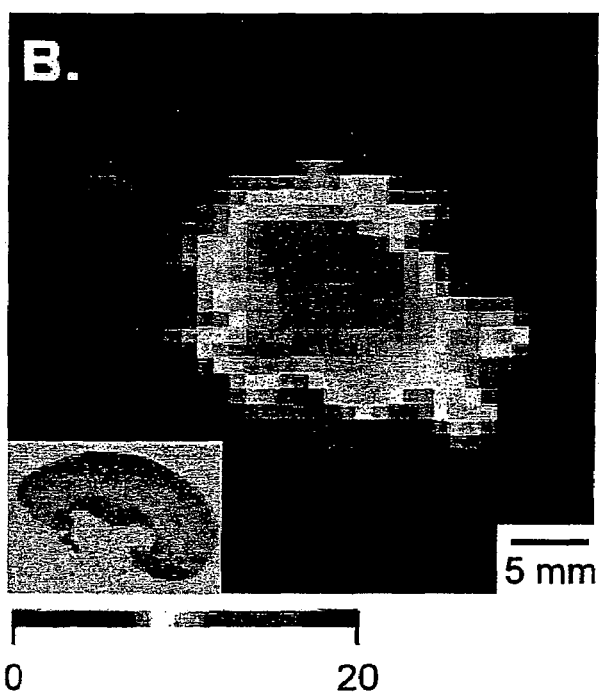
Figure 12B:
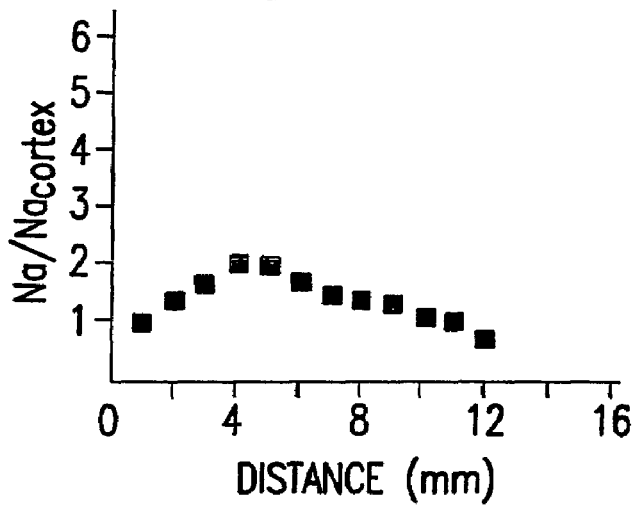

Experimental acute hydronephrosis: Rats, about three-month-old, with a unilateral ligation of the left ureter developed a severe hydronephrosis in the left kidney. The plasma creatinine levels in these rats (0.61±0.04 mg/dL, n=5) measured 2 days after inducing hydronephrosis, were similar to those measured in plasma of control rats (0.54±0.03 mg/dL, n=10). $^1$H MR imaging of the obstructed kidney indicated an increase in size of ~30%. The distribution of sodium, recorded by $^{23}$Na MRI, was very different form that of control and of the spontaneous hydronephrotic kidneys (FIG. 11B). Pixel by pixel analysis along the corticomedullary axis indicated a mild linear increase in sodium signal from the cortex to the outer medulla followed by a rapid decrease in the sodium signal from the outer medulla toward the papilla, to a level similar—and, in two kidneys, below that of the cortex (FIG. 12B). The extent of the cortico-outermedullary sodium gradient (0.23±0.04 a.u×mm$^{-1}$, n=5) was significantly lower compared to that of control kidneys (p=0.01).

Figure 13F:
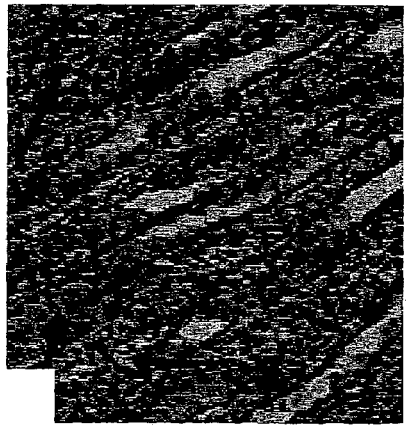

Histology of the acutely obstructed kidneys revealed a reduction in the parenchyma thickness in the same manner as in the spontaneous hydronephrotic kidneys (4±1 mm, n=5). However, in contrast to the spontaneous hydronephrosis, the microscopic inspection indicated a vast cortical and medullar tubular dilation and atrophy (FIGS. 13C, 13F and 13I).

Figure 12C:
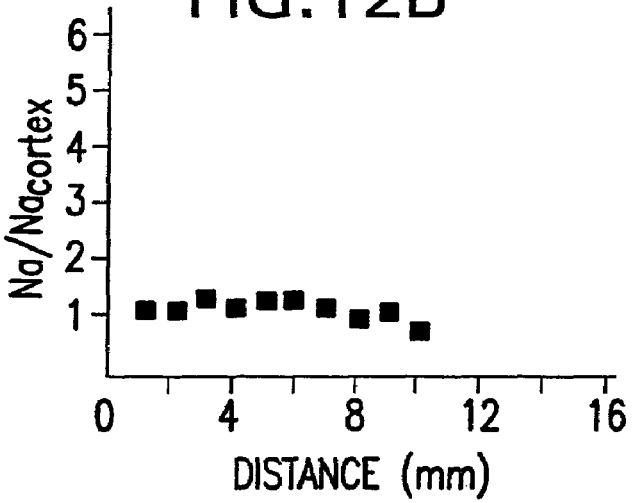

The functional ability of the hydronephrotic kidney to maintain the sodium gradient was compared with that of normal kidney under diuresis induced by furosemide. This loop diuretic is known to dissipate the corticomedullary sodium gradient by inhibition of the Na$^+$/2Cl$^-$/K$^+$ cotransporter in the outer medullar thick ascending limb which participates in the build-up and maintenance of the sodium corticomedullary gradient. Under furosemide steady state diuresis the inner- and outer medulla sodium decreased while that of the cortex increased leading to an almost complete cancellation of the corticomedullary sodium gradient (FIG. 12C). The cortico-outer medullar sodium gradient during furosemide diuresis in the acute hydronephrotic kidneys (0.10±0.01 a.u×mm$^{-1}$, n=7) was significantly lower (p=0.006) than that observed in the spontaneous hydronephrotic kidneys, indicating a more sever reduction in the kidney function due to the former obstruction.

Discussion: Different MRI protocols reveal unique renal structural and functional aspects. In $T_1$ weighted MRI of the kidney the presence or absence of a contrast between the cortex and the medulla: the corticomedullary differentiation (CMD), Stark, D. D., and W. G. Bradley jr. *Magnetic resonance imaging.* St. Louis: Mosby year book, 1992, serve, respectively, to determine renal hydration or to identify a variety of renal diseases including acute tubular necrosis, glomerulonephritis, acute and chronic renal failure, renal artery stenosis, renal venous or arterial occlusion, hydronephrosis, and transplant rejection, Marotti M, H. H., Terrier F, McAninch J W, Thuroff J W. MR in renal disease: importance of cortical-medullary distinction. *Magn Reson Med* 5: 160–172, 1987; and Morehouse, H. T., E. Levee, L. States, J. Zimmerman, J. H. Newhouse, and E. S. J. Amis. MRI anatomy of the rat kidney at 1.5 T in different states of hydration. *Magn. Reson. Imaging* 13: 81–88, 1995. The loss of CMD is, however, a non-specific indicator of a renal pathologic state. In order to characterize specific renal pathologies by MRI more sophisticated MRI methods were applied, such as a breath hold, phase-contrast method, Myers, B. D., F. G. Sommer, K. Li, S. Tomlanovich, N. Pelc, C. McDonnell, E. contrast method, Pagtalunan, L. Newton, and R. Jamison. Determination of blood flow to the transplanted kidney. A novel application of phase-contrast, cine magnetic resonance imaging. *Transplantation* 57: 1445–1450, 1994, and intravoxel incoherent motion imaging (IVIM) with respiratory triggering, Powers, T. A., C. H. Lorenz, G. E. Holburn, and R. R. Price. Renal artery stenosis: in vivo perfusion MR imaging. *Radiology* 178:

543–548, 1991. However, the most useful application of MRI involved dynamic contrast enhanced monitoring Knesplova, L., and G. P. Krestin. Magnetic resonance in the assessment of renal function. Eur. Radiol. 8: 201–211, 1998, as it provides a detailed morphological information and indirectly reflects the functional status of the renal vasculature, renal perfusion and tubular concentration ability.

The main function of the kidney in maintaining fluid homeostasis depends on the corticomedullary sodium concentration gradient. Therefore, by the present invention this gradient is monitored directly, by $^{23}$Na MRI; this provides the essential quantitative assessment of renal function, and can yield specific diagnosis of renal pathologies. The extensive extracellular volume of the kidney (including the intravascular and the intraluminal space), as well as, the marked increase in sodium content due to the countercurrent mechanism enabled selectively imaging renal sodium at a relatively high spatial resolution (in plane spatial resolution of less than 1 mm$^2$). With this resolution the present invention enabled observation in great detail of the variation in the sodium concentration in different regions of the kidney. Analysis of the signal intensity along the corticomedullary axis, pixel by pixel, clearly showed that the nature of this increase is linear rather than exponential, resulting in a ~4-fold ratio between the average sodium concentration in the inner medulla compared to that in the cortex. The 4-fold ratio found here is close to that found by sodium MRI of the exposed rabbit kidney, Wolff, S. D., J. Eng, B. A. Berkowitz, S. James, and R. S. Balaban. Sodium-23 nuclear magnetic resonance imaging of the rabbit kidney in vivo. Am. J. Physiol. 258: F1125–F1131, 1990, and within the range found in previous studies, using invasive methods (2.5–5), Azar, S., L. Tobian, and M. Ishii. Prolonged water diuresis affecting solutes and interstitial cells of renal papilla. Am. J. Physiol. 221: 75–79, 1971; Bengele, H. H., R. S. Mathias, J. H. Perkins, and E. A. Alexander. Urinary concentrating defect in aged rat. Am. J. Physiol. 240: F147–F150, 1981; Buerkert, J., D. Martin, J. Prasad, and D. Trigg. Role of deep nephrons and the terminal collecting duct in mannitol-induced diuresis. Am. J. Physiol. 240: F411–F422, 1981; Gennari, F. J., C. Johns, C. R. Caflisch, and S. Cortell. Dissociation of saline-induced natiuresis from urea washout in the rat. Am. J. Physiol. 241: F250–F256, 1981; Jamison, R. L. The renal concentrating mechanism: micropuncture studies of the renal medulla. Fed. Proc. 42: 2392–2397, 1983; Martinez-Maldonado, M., G. Eknoyan, and W. N. Suki. Influence of volume expansion on renal diluting capacity in the rat. Clin. Sci. Mol. Med. 46: 331–345, 1974; Pallone, T. L., Y. Yagil, and R. L. Jamison. Effect of small-solute gradients on transcapillary fluid movement in renal inner medulla. Am. J. Physiol. 257: F547–F553, 1989; and Valtin, H. Sequensration of urea and non urea solutes in renal tissues of rats with hereditary hypothalamic diabetes insipidus: effect of vasopressin and dehydration on countercurrent mechanism. J. Clin. Invest. 45: 337–345, 1966.

This finding is in contrast to the exponential sodium gradient that was reported by Koepsell et al., Koepsell, H., W. A. P. Nicholson, W. Kriz, and H. J. Hohling. Measurements of exponential gradients of sodium and chlorine in the rat kidney medulla using electron microprobe. Pflugers Arch. 350: 167–184, 1974, that was also predicted by mathematical modeling Edwards, A., M. J. Delong, and T. L. Pallone. Interstitial water and solute recovery by inner medullary vasa recta. Am. J. Physiol. Renal Physiol. 278: F257–F269, 2000. The exponential sodium gradient in that study resulted in a ~12 fold higher sodium concentration in the papilla tip than that in the cortex.

Mapping the sodium distribution in the kidney non-invasively at high resolution, according to the method of the present invention, enabled following changes in this distribution induced by hydronephrosis, which is a common problem treated by urologist. Characteristically, urinary tract obstruction is associated with dilations of the urinary tract, reduction in parenchyma thickness and decreased renal function. Since urine and plasma composition cannot indicate unilateral hydronephrosis, additional methods are required to diagnose this pathological state. Dynamic contrast enhanced images of the hydronephrotic kidney revealed the presence of obstruction as was shown by other studies, Wen, J. G., Y. Chen, S. Ringgaard, J. Frokiaer, T. M. Jorgensen, H. Stodkilde-Jorgensen, and J. C. Djurhuus. Evaluation of renal function in normal and hydronephrotic kidneys in rats using gadolinium diethylenetetramine-pentaacetic acid enhanced dynamic magnetic resonance imaging. J. Urol. 163: 1264–1270, 2000. Although this method was capable to differentiate between partial and complete obstruction, it gave limited information about the residual function of the obstructed kidney, as the contrast agent could not be washed out through the obstructed ureter.

A moderate positive correlation between the apparent diffusion coefficient (ADC) values and glomerular filtration rate was found in the hydronephrotic versus control kidneys using diffusion-weighted MR imaging Toyoshima, S., K. Noguchi, H. Seto, M. Shimizu, and N. Watanabe. Functional evaluation of hydronephrosis by diffusion-weighted MR imaging. Relationship between apparent diffusion coefficient and split glomerular filtration rate. Acta. Radiol. 41: 642–646, 2000. However, the change in the ADC value in the dysfunctional hydronephrotic kidneys relative to the functional normal ones was found to be very small.

In this $^{23}$Na MRI study of the intact kidney, the sodium distribution was markedly different between obstructed and control kidneys. In both acute and spontaneous hydronephrosis, the kidneys did not exhibit a linear corticomedullary sodium gradient mainly due to the marked reduction in the inner medulla sodium level, which was correlated with the vast parenchyma atrophy in this region. Both acute and spontaneous hydronephrotic kidneys maintained a linear sodium gradient along the cortico-outer medullar axis, however, the extent of this gradient was significantly lower in the acute obstructed kidney whereas in the control and the spontaneous hydronephrotic kidneys the sodium gradient along the cortico-outer medullar axis was similar.

Although no significant change was observed in the total size of the parenchyma between the acute and the spontaneous hydronephrotic kidney, a significant difference was observed at the microscopic histological findings. Namely, a clear tubular damage was observed in the acute hydronephrotic kidneys and not in the spontaneous ones. This lack of differentiation in the macro level infers the limitation of solely anatomical imaging and the necessity of functional imaging to differentiate between these two types of hydronephrosis.

The specificity of sodium MRI as a functional imaging method, according to the present invention, was further demonstrated by comparing the sodium distribution along the corticomedullary axis in the hydronephrotic kidneys with that in the furosemide induced diuretic kidneys. Furosemide, a loop diuretic agent, is known to block the Na$^+$/2Cl$^-$/K$^+$ cotransporter located in the apical membrane of the thick segment of the medullar ascending limb. This cotransporter, together with the Na$^-$/K$^+$/ATPase pump in the basal membrane, extrudes sodium from the tubule to the interstitium. Thus furosemide inhibits sodium reabsorption in the outer medulla thick ascending limb and thereby reduces the corticomedullary sodium gradient, Puschett, J. B. Pharmacological classification and renal actions of diuretics. *Cardiology* 84: 4–13, 1994. Thus, the diuretic state induced by this agent served as a model for a kidney that lost its concentration functional ability. Interestingly, despite the vast observed histological damage in the remaining parenchyma of the acute hydronephrotic kidney, part of its function was maintained, as indicated by the 2-fold higher cortico-outer medullar sodium gradient found in these kidneys compared to that in the diuretic kidney.

Figure 14:
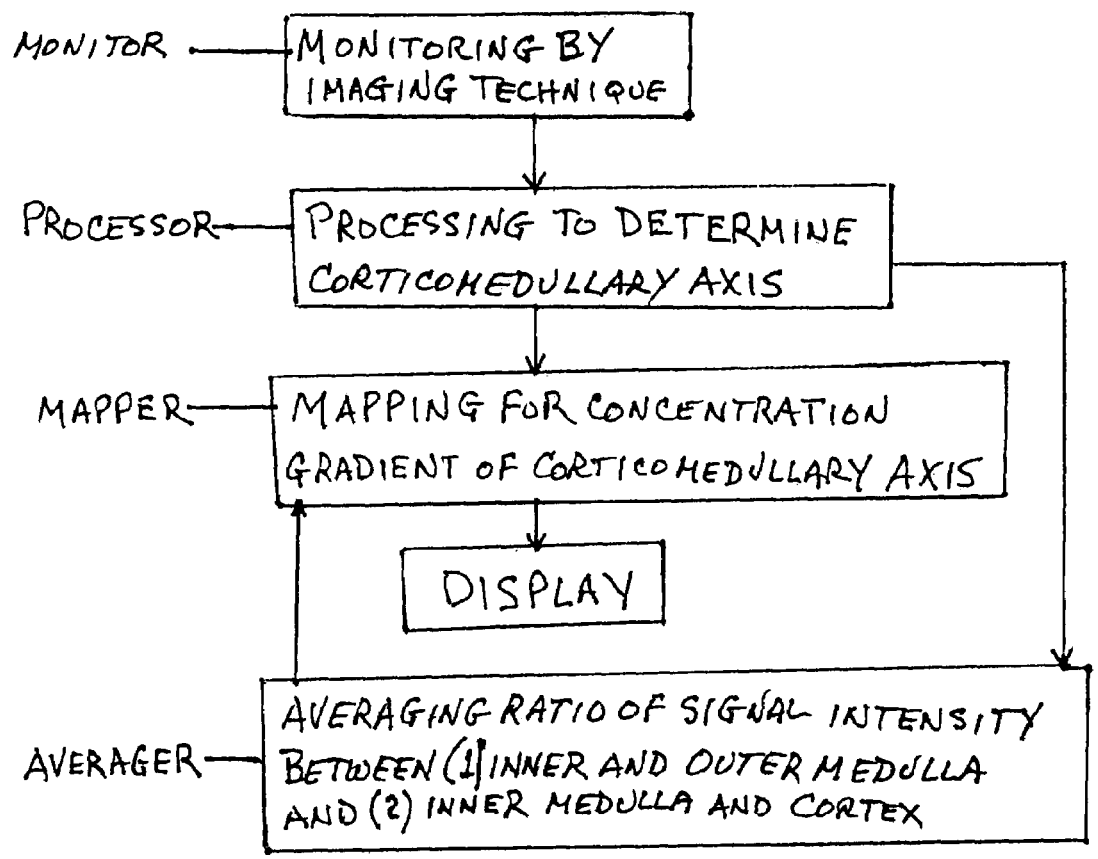
FIG. 14 is a block diagram showing the apparatus used in the present invention.

The apparatus of the invention is shown in FIG. 14, and consists of a monitor to effect the monitoring by an imaging technique. The output of the monitor is fed to a processor for processing to determine the corticomedullary axis of the kidney, and the output signals are passed to a mapper for mapping the concentration gradient of the corticomedullary axis. Also, the processor feeds its output to an averager for averaging the ratio of signal intensity between (1) the inner medulla and outer medulla and (2) the inner and cortex. The output of the averager is fed to the mapper and displayed in the display, along with the concentration gradient of the corticomedullary axis.

Although the invention has been described with respect to preferred embodiments, nevertheless changes and modifications will be evident to those skilled in the art from the disclosure and teachings herein. Such changes and modifications that do not depart from the teachings herein are deemed to fall within the purview of the invention as claimed.

What is claimed is:

1. A method for monitoring a kidney comprising the steps of:
   a. monitoring the corticomedullary sodium concentration gradient in a kidney characterized by a cortex, an outer medulla contiguous to the cortex on one side and to an inner medulla on the opposite side thereto, by an MRI imaging technique, to obtain dynamic images;
   b. processing the obtained images to quantitatively determine, pixel by pixel of the images, the concentration of sodium along the corticomedullary axis of the kidney;
   c. mapping the sodium distribution at high resolution to indicate the sodium concentration gradient of the corticomedullary axis of the kidney; and
   d. determining from the slope of the sodium concentration gradient of the corticomedullary axis indications of any obstruction in the kidney and the residual functioning of the kidney.

2. The method of claim 1 including the further step of injecting a diuretic selected from the group consisting of mannitol and furosemide.

3. A method for monitoring a kidney comprising the steps of:
   a. monitoring the corticomedullary sodium concentration gradient in a kidney characterized by a cortex, an outer medulla contiguous to the cortex on one side and to an inner medulla on the opposite side thereto, by an MRI imaging technique, to obtain dynamic images;
   b. processing the obtained images to quantitatively determine, pixel by pixel of the images, the concentration of sodium along the corticomedullary axis of the kidney;
   c. mapping the sodium distribution at high resolution to indicate the sodium concentration gradient of the corticomedullary axis of the kidney; and
   d. determining from the slope of the sodium concentration gradient of the corticomedullary axis indications of any obstruction in the kidney and the residual functioning of the kidney, wherein the monitoring is carried out using $^{23}$Na MRI.

4. The method of claim 3 including the further step of determining the existence of any hydronephrosis in the kidney.

5. The method of claim 4 including the further step of distinguishing between spontaneous hydronephrosis and acute hydronephrosis.

6. The method of claim 5 including the further steps of detecting any obstruction in the kidney, and measuring the extent of residual functioning of the obstructed kidney.

7. The method of claim 3 including the further step of conducting the imaging at high spatial resolution.

8. The method of claim 3 including the further steps of defining a region of interest (ROI) of the kidney from coronal images recorded prior to the imaging by $^{23}$Na MRI, averaging digitized pixel intensity for the ROI, assessing the sodium gradient by averaging the ratio of sodium signal intensity between the inner and outer medulla of the kidney, and between the inner medulla and the cortex of the kidney, and analyzing pixel by pixel the ROI to assess behavior of the sodium signal along the corticomedullary axis of the kidney.

9. A method for monitoring a kidney comprising the steps of:
   a. monitoring the corticomedullary sodium concentration gradient in a kidney characterized by a cortex, an outer medulla contiguous to the cortex on one side and to an inner medulla on the opposite side thereto, by an MRI imaging technique, to obtain dynamic images;
   b. processing the obtained images to quantitatively determine, pixel by pixel of the images, the concentration of sodium along the corticomedullary axis of the kidney;
   c. mapping the sodium distribution at high resolution to indicate the sodium concentration gradient of the corticomedullary axis of the kidney; and
   d. determining from the slope of the sodium concentration gradient of the corticomedullary axis indications of any obstruction in the kidney and the residual functioning of the kidney, wherein the imaging is conducted using 3D magnetic resonance imaging.

10. Apparatus for monitoring a kidney comprising:
    a. a monitor for determining the corticomedullary sodium concentration gradient in a kidney, characterized by a cortex, an outer medulla contiguous to the cortex on one side and to an inner medulla on the opposite side thereto, by an MRI imaging technique, to obtain dynamic images;
    b. a processor for processing the obtained images to quantitatively determine, pixel by pixel of the images, the concentration of sodium along the corticomedullary axis of the kidney;
    c. a mapper for mapping the sodium distribution at high resolution to indicate the sodium concentration gradient of the corticomedullary axis of the kidney and for determining from the slope of the corticomedullary axis indications of an obstruction in the kidney and the residual functioning thereof.

11. Apparatus according to claim 10 further including a display for portraying maps of the sodium distribution.

12. The apparatus of claim 10 wherein the imaging is conducted at high spatial resolution.

13. The apparatus of claim 10 further comprising a diuretic which is adapted to be injected, wherein the diuretic is selected from the group consisting of mannitol and furosemide.

14. Apparatus for monitoring a kidney comprising:
a. a monitor for determining the corticomedullary sodium concentration gradient in a kidney, characterized by a cortex, an outer medulla contiguous to the cortex on one side and to an inner medulla on the opposite side thereto, by an MRI imaging technique, to obtain dynamic images;
b. a processor for processing the obtained images to quantitatively determine, pixel by pixel of the images, the concentration of sodium along the corticomedullary axis of the kidney;
c. a mapper for mapping the sodium distribution at high resolution to indicate the sodium concentration gradient of the corticomedullary axis of the kidney and for determining from the slope of the corticomedullary axis indications of an obstruction in the kidney and the residual functioning thereof, wherein $^{23}$Na MRI is used for the imaging technique.

15. The apparatus of claim 14 wherein the existence of any hydronephrosis in the kidney is determined.

16. The apparatus of claim 15 wherein spontaneous hydronephrosis and acute hydronephrosis are distinguished.

17. The apparatus of claim 16 wherein any obstruction in the kidney is detected, and the extent of residual functioning of the obstructed kidney is measured.

18. The apparatus of claim 14 wherein a region of interest (ROI) of the kidney is defined from coronal images recorded prior to the imaging by $^{23}$Na MRI, a digitized pixel intensity for the ROI is averaged, the sodium gradient is assessed by averaging the ratio of sodium signal intensity between the inner and outer medulla of the kidney, and between the inner medulla and the cortex of the kidney, and the ROI is analyzed pixel by pixel to assess behavior of the sodium signal along the corticomedullary axis of the kidney.

19. Apparatus for monitoring a kidney comprising:
a. a monitor for determining the corticomedullary sodium concentration gradient in a kidney, characterized by a cortex, an outer medulla contiguous to the cortex on one side and to an inner medulla on the opposite side thereto, by an MRI imaging technique, to obtain dynamic images;
b. a processor for processing the obtained images to quantitatively determine, pixel by pixel of the images, the concentration of sodium along the corticomedullary axis of the kidney;
c. a mapper for mapping the sodium distribution at high resolution to indicate the sodium concentration gradient of the corticomedullary axis of the kidney and for determining from the slope of the corticomedullary axis indications of an obstruction in the kidney and the residual functioning thereof, wherein the imaging is conducted using 3D magnetic resonance imaging.

* * * * *

UNITED STATES PATENT AND TRADEMARK OFFICE
CERTIFICATE OF CORRECTION

PATENT NO.         : 7,146,204 B2  
APPLICATION NO. : 10/974117  
DATED                  : December 5, 2006  
INVENTOR(S)       : Hadassa Degani and Nimrod Maril It is certified that error appears in the above-identified patent and that said Letters Patent is hereby corrected as shown below:

Title Page  
INID 75  
Change inventor's name from "Maril Nimrod" to --Nimrod Maril--.

Signed and Sealed this

Tenth Day of April, 2007

JON W. DUDAS  
*Director of the United States Patent and Trademark Office*